United States Patent
Ebisawa et al.

(10) Patent No.: US 9,540,459 B2
(45) Date of Patent: Jan. 10, 2017

(54) PRODUCTION METHOD OF OLEFIN POLYMER AND OLEFIN POLYMERIZATION CATALYST

(71) Applicant: MITSUI CHEMICALS, INC., Tokyo (JP)

(72) Inventors: Ikuko Ebisawa, Chiba (JP); Hideo Kitagawa, Kawasaki (JP); Takashi Yukita, Chiba (JP); Masahiro Yamashita, Chiba (JP); Kouji Takeda, Ichihara (JP); Hiromu Kaneyoshi, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/773,638

(22) PCT Filed: Mar. 11, 2014

(86) PCT No.: PCT/JP2014/056294
§ 371 (c)(1),
(2) Date: Sep. 8, 2015

(87) PCT Pub. No.: WO2014/142111
PCT Pub. Date: Sep. 18, 2014

(65) Prior Publication Data
US 2016/0039952 A1    Feb. 11, 2016

(30) Foreign Application Priority Data
Mar. 12, 2013 (JP) ................................. 2013-049092

(51) Int. Cl.
| | | |
|---|---|---|
| C08F 4/6592 | (2006.01) | |
| C08F 10/04 | (2006.01) | |
| C08F 110/06 | (2006.01) | |
| C08F 10/06 | (2006.01) | |
| C08F 4/659 | (2006.01) | |
| C07F 7/00 | (2006.01) | |

(52) U.S. Cl.
CPC ............... *C08F 10/06* (2013.01); *C07F 7/00* (2013.01); *C08F 4/65912* (2013.01); *C08F 4/65927* (2013.01); *C08F 110/06* (2013.01)

(58) Field of Classification Search
CPC ............. C08F 4/65927; C08F 4/65908; C08F 4/65912; C08F 10/04; C08F 110/06
See application file for complete search history.

(56) References Cited

U.S. PATENT DOCUMENTS

| | | |
|---|---|---|
| 4,960,878 A | 10/1990 | Malpass |
| 4,990,640 A | 2/1991 | Tsutsui |
| 5,036,034 A | 7/1991 | Ewen |
| 5,041,584 A | 8/1991 | Malpass |
| 5,225,500 A | 7/1993 | Razavi |
| 5,278,119 A | 1/1994 | Turner |
| 5,321,106 A | 6/1994 | LaPointe |
| 5,416,228 A | 5/1995 | Elder |
| 5,519,100 A | 5/1996 | Elder |
| 5,663,249 A | 9/1997 | Ewen |

(Continued)

FOREIGN PATENT DOCUMENTS

| | | |
|---|---|---|
| CA | 2350563 | 5/2000 |
| CN | 1156728 A | 8/1997 |

(Continued)

OTHER PUBLICATIONS

International Search Report dated Jun. 3, 2014 filed in PCT/JP2014/056294.
Angew. Chem. Int. Ed. Engl., 24, No. 6, 1985, pp. 506-509.
J. Am. Chem. Soc., 110, 1988, pp. 6255-6256.
Chinese Office Action dated Jun. 8, 2016 issued in the corresponding Chinese patent application No. 201480023882.1.

*Primary Examiner* — Caixia Lu
(74) *Attorney, Agent, or Firm* — Rankin, Hill & Clark LLP

(57) ABSTRACT

To provide a method of efficiently affording olefin polymers having a high molecular weight and a high melting point even under industrially advantageous high-temperature conditions. A production method of an olefin polymer to solve the above problem includes polymerizing monomer(s) including at least one α-olefin having 3 or more carbon atoms at 50° C. to 200° C. in the presence of an olefin polymerization catalyst including; (A) a crosslinked metallocene compound represented by General Formula [I] below; and (B) at least one compound selected from (b-1) an organoaluminum oxy-compound, (b-2) a compound that forms an ion pair by reacting with the crosslinked metallocene compound (A), and (b-3) an organoalunimum compound.

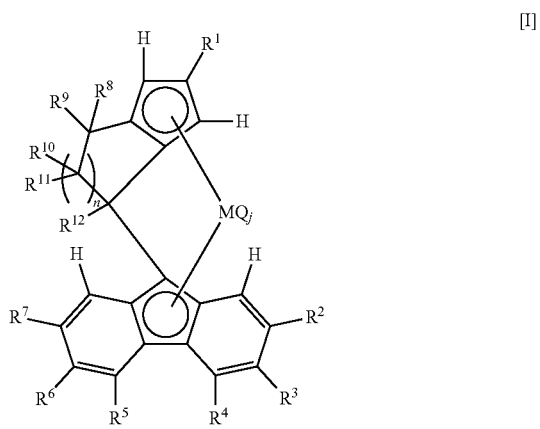

24 Claims, No Drawings

(56) References Cited

U.S. PATENT DOCUMENTS

| | | |
|---|---|---|
| 5,883,202 A | 3/1999 | Ewen |
| 6,004,897 A | 12/1999 | Yoshida |
| 6,297,333 B1 | 10/2001 | Yoshida |
| 2005/0228155 A1 | 10/2005 | Mori |
| 2006/0161013 A1 | 7/2006 | Kawai |
| 2008/0038498 A1* | 2/2008 | Itakura .................. C08F 10/00 428/35.7 |
| 2008/0220193 A1 | 9/2008 | Hirota |
| 2009/0069523 A1 | 3/2009 | Funaya |
| 2009/0317615 A1 | 12/2009 | Hashizume |
| 2010/0234810 A1 | 9/2010 | Hashizume |
| 2015/0239996 A1* | 8/2015 | Funaya .................. C08F 10/00 526/127 |
| 2015/0252123 A1* | 9/2015 | Funaya ............... C08F 4/65927 526/170 |

FOREIGN PATENT DOCUMENTS

| | | |
|---|---|---|
| CN | 1327448 A | 12/2001 |
| CN | 101087821 A | 12/2007 |
| CN | 101501128 A | 8/2009 |
| CN | 101809052 A | 8/2010 |
| EP | 1902062 A2 | 3/2008 |
| JP | 1501950 | 7/1989 |
| JP | 1502036 | 7/1989 |
| JP | 2024701 A2 | 1/1990 |
| JP | 278687 | 3/1990 |
| JP | 2167305 A2 | 6/1990 |
| JP | 3103407 A2 | 4/1991 |
| JP | 3179005 A2 | 8/1991 |
| JP | 3179006 A2 | 8/1991 |
| JP | 3193796 A2 | 8/1991 |
| JP | 3207703 A2 | 9/1991 |
| JP | 3207704 A2 | 9/1991 |
| JP | 6122718 A2 | 5/1994 |
| JP | 2000212194 A2 | 8/2000 |
| JP | 2002529555 T2 | 9/2002 |
| JP | 200451676 | 2/2004 |
| JP | 2004161957 A2 | 6/2004 |
| JP | 2004168744 A2 | 6/2004 |
| JP | 2004189666 A2 | 7/2004 |
| JP | 2007302853 A2 | 11/2007 |
| JP | 2007302854 A2 | 11/2007 |
| JP | 2009500371 T2 | 1/2009 |
| JP | 2012236994 A2 | 12/2012 |
| WO | 8805793 A1 | 8/1988 |
| WO | 0127124 | 4/2001 |
| WO | 2004046205 A1 | 6/2004 |
| WO | 2006068308 A1 | 6/2006 |
| WO | 2007116709 A1 | 10/2007 |
| WO | 2012147995 A1 | 11/2012 |

* cited by examiner

PRODUCTION METHOD OF OLEFIN POLYMER AND OLEFIN POLYMERIZATION CATALYST

TECHNICAL FIELD

The present invention relates to a production method of an olefin polymer and an olefin polymerization catalyst.

BACKGROUND ART

In recent years, metallocene compounds have been known as homogeneous catalysts for olefin polymerization. With regard to polymerizing olefins (in particular, polymerizing α-olefins) by use of metallocene compounds, since isotactic polymerization has been reported by W. Kaminsky et al., many studies have been conducted for improvement of stereoregularity and polymerization activity (Non-Patent Document 1).

It is known, in α-olefin polymerization by use of metallocene compounds, that the stereoregularity and molecular weights of olefin polymers greatly vary by the introduction of substituents to the cyclopentadienyl ring ligands of the metallocene compounds or by the crosslinking the two cyclopendienyl rings.

For example, when metallocene compounds having a ligand in which a cyclopentadienyl ring and a fluorenyl ring are crosslinked is used as a polymerization catalyst, in terms of the stereoregularity of polymers, dimethylmethylene(cyclopentadienyl)(fluorenyl)zirconium dichloride affords syndiotactic polypropylene (Non-Patent Document 2), dimethylmethylene(3-methylcyclopentadienyl)(fluorenyl) zirconium dichloride, which has a methyl group attached to the 3 position of a cyclopentadienyl ring, affords hemi-isotactic polyprolylene (Patent Document 1); and dimethylmethylene(3-tert-butylcyclopentadienyl)(fluorenyl)zirconium dichloride, which has a tert-butyl group attached to the 3 position of a cyclopentadienyl ring, affords isotactic polyprolylene (Patent Document 2).

In modifying these metallocene compounds, it is possible to obtain high melting points, an indicator of the stereoregularity of a polymer, and to obtain high molecular weight. Also, it is possible to produce a polymer with a high melting point and a sufficiently high molecular weight.

CITATION LIST

Patent Literature

Patent Document 1: JP-A-H03-193796
Patent Document 2: JP-A-H06-122718

Non-Patent Literature

Non-Patent Document 1: Angew. Chem. Int. Ed. Engl., 24, 507 (1985)
Non-Patent Document 2: J. Am. Chem. Soc., 110, 6255 (1988)

SUMMARY OF THE INVENTION

Problems to be Solved by the Invention

However, a polymer having a high melting point and a sufficiently high molecular weight is not enough to develop a polymerization catalyst by way of high polymerization activity. Thus, a producing method has been strongly demanded which gives a polymer having a relatively high melting point and a high molecular weight by way of high productivity.

Also, in making possible the industrial production of such olefin polymers, it would be desirable to produce olefin polymers having the above properties at a temperature of not lower than room temperature, preferably higher than room temperature, but no such polymerization catalyst was known.

The present invention is created to resolve the above issue, with a purpose of efficiently producing an olefin polymer having a high melting point and a high molecular weight under high temperature which is advantageous in industrial processes and producing an olefin polymerization catalyst.

Means to Solve the Problems

The present inventors have intensively studied to solve the above problem and have discovered that the problem can be solved by a production method of olefin polymer by the use of olefin polymerization catalyst comprising a novel metallocene compound having a specific structure, to complete the present invention.

The production method of an olefin polymer in the present invention to solve the above problem comprises
polymerizing at least one selected from α-olefins having 3 to 20 carbon atoms at not less than 50° C. and not more than 200° C. in the presence of an olefin polymerization catalyst comprising:
(A) a crosslinked metallocene compound represented by General Formula [I] below; and
(B) at least one compound selected from
(b-1) an organoaluminum oxy-compound,
(b-2) a compound that forms an ion pair by reacting with the crosslinked metallocene compound (A), and
(b-3) anorganoalunimum compound.

[Chem. 1]

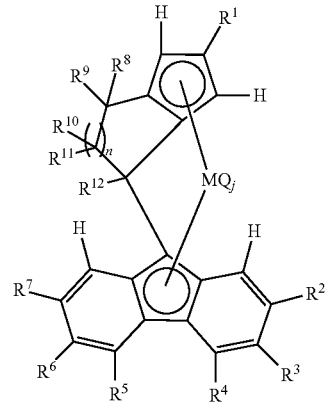

[I]

(In the formula, $R^1$ is an adamantyl group derivative; $R^2$ and $R^7$ are selected from a hydrocarbon group, a silicon-containing group, and a halogen-containing hydrocarbon group; $R^3$ and $R^6$ are hydrogen atoms; $R^4$, $R^5$, $R^8$, $R^9$, $R^{10}$, $R^{11}$, and $R^{12}$ are selected from a hydrogen atom, a hydrocarbon group, a silicon-containing group, a halogen atom, and a halogen-containing hydrocarbon group and may be the same or different from each other, and adjacent substituents among $R^4$, $R^5$, $R^8$, $R^9$, $R^{10}$, $R^{11}$, and $R^{12}$ may combine to form a ring; n is an integer between 1 and 3; N is a Group 4 transition metal; Q is a halogen atom, a hydrocarbon group, an anionic ii a neutral ligand that is bondable with a lone pair and may be the same or different from each other; and j is an integer between 1 and 4.)

In the olefin polymer production method of the present invention, $R^1$ is preferably a 1-adamantyl group in the above Formula [I].

In the olefin polymer production method of the present invention, $R^2$ and $R^7$ are preferably hydrocarbon groups having 4 to 10 carbon atoms in the above Formula [I].

In the olefin polymer production method of the present invention, $R^4$ and $R^5$ are preferably hydrogen atoms in the above Formula [I].

In the olefin polymer production method of the present invention, $R^{12}$ is preferably a hydrocarbon group having 1 to 20 carbon atoms in the above Formula [I].

In the olefin polymer production method of the present invention, $R^8$ to $R^{11}$ are preferably hydrogen atoms or hydrocarbon groups having 1 to 20 carbon atoms in the above Formula [I].

In the olefin polymer production method of the present invention, $R^{10}$ and $R^{11}$ are preferably hydrogen atoms in the above Formula [I].

In the olefin polymer production method of the present invention, $R^8$ and $R^9$ are hydrocarbon groups having 1 to 20 carbon atoms in the above Formula [I].

In the olefin polymer production method of the present invention, n is preferably 1 in the above Formula [I].

In the olefin polymer production method of the present invention, at least one of the above α-olefins having 3 or more carbon atoms is preferably propylene.

In the olefin polymer production method of the present invention, the olefin polymerization activity under hydrogen-free conditions is preferably not less than 50 kg/mmol-M/h and not more than 1,000,000 kg/mmol-M/h, and the olefin polymer preferably satisfies both of the requirements (i) and (iii) below.

(i) Propylene content (P) is 51 mol %≤P≤100 mol %.

(iii) Intrinsic viscosity [η] in decalin at 135° C. is 1.0 (dl/g)≤[η]≤10 (dl/g).

In the olefin polymer production method of the present invention, the peak melting point (A) obtained from the differential scanning calorimetry (DSC) of the olefin polymer is preferably 130° C.≤A≤155° C.

In the olefin polymer production method of the present invention, the olefin polymerization activity is preferably not less than 1,000 kg/mmol-M/h and not more than 1,000,000 kg/mmol-M/h, and the olefin polymer preferably satisfies both of the requirements (i) and (iii) below.

(i) Ethylene content (E) is 1 mol %≤E≤10 mol %, and propylene content (P) is 90 mol %≤P≤99 mol % (provided that (E)+(P)=100 mol %).

(iii) Melt mass-flow rate (MFR; g/10 min.) measured under the conditions of ASTM D1238 is 0.1≤MFR≤150.

In the olefin polymer production method of the present invention, the peak melting point (A) obtained from the differential scanning calorimetry (DSC) of the olefin polymer is preferably 110° C.≤A≤135° C.

In the olefin polymer production method of the present invention, the above olefin polymerization catalyst preferably further comprises a carrier (C).

Further, the olefin polymerization catalyst (A) of the present invention represented by General Formula [I] below.

[Chem. 2]

[I]

(In the formula, $R^1$ is an adamantyl group derivative; $R^2$ and $R^7$ are selected from a hydrocarbon group, a silicon-containing group, and a halogen-containing hydrocarbon group; $R^3$ and $R^6$ are hydrogen atoms; $R^4$, $R^5$, $R^8$, $R^9$, $R^{10}$, $R^{11}$, and $R^{12}$ are selected from a hydrogen atoms, a hydrocarbon group, a silicon-containing group, a halogen atoms, and a halogen-containing hydrocarbon group, and may be the same or different from each other, and adjacent substituents among $R^4$, $R^5$, $R^8$, $R^9$, $R^{10}$, $R^{11}$, and $R^{12}$ may combine to form a ring; n is an integer between 1 and 3; M is a Group 4 transition metal; Q is a halogen atom, a hydrocarbon group, an anionic ligand, or a neutral ligand that is bondable with a lone pair and may be the same or different from each other; and j is an integer between 1 and 4.)

In the olefin polymer production method of the present invention, $R^1$ is preferably a 1-adamantyl group in the above Formula [I].

In the olefin polymerization catalyst of the present invention, $R^2$ and $R^7$ are preferably hydrocarbon groups having 4 to 10 carbon atoms in the above Formula [I].

In the olefin polymerization catalyst of the present invention, $R^4$ and $R^5$ are preferably hydrogen atoms in the above Formula [I].

In the olefin polymerization catalyst of the present invention, $R^{12}$ is preferably a hydrocarbon group having 1 to 20 carbon atoms in the above Formula [I].

In the olefin polymerization catalyst of the present invention, $R^8$ to $R^{11}$ are preferably hydrogen atoms or hydrocarbon groups having 1 to 20 carbon atoms in the above Formula [I].

In the olefin polymerization catalyst of the present invention, $R^{10}$ and $R^{11}$ are preferably hydrogen atoms in the above Formula [I].

In the olefin polymerization catalyst of the present invention, $R^8$ and $R^9$ are preferably hydrocarbon groups having 1 to 20 carbon atoms in the above Formula [I].

In the olefin polymerization catalyst of the present invention, n is preferably 1 in the above Formula [I].

Advantageous Effects of Invention

According to the present invention, an olefin polymer can be efficiently produced by using an olefin polymerization catalyst comprising a useful, novel metallocene compound of a specific structure. Further, the present invention provides an olefin polymerization catalyst that produces an olefin polymer through high polymerization activity.

DESCRIPTION OF EMBODIMENTS

The method of producing an olefin polymer according to the present invention is described from hereunder. Descriptions are given for a crosslinked metallocene compound represented by General Formula [I] of the present invention (hereinafter referred to as metallocene compounds (A)); an example of the preferred metallocene compounds (A); the production method of metallocene compounds (A); preferred forms of metallocene compounds (A) when it is provided to the olefin polymerization catalyst; and the production method of an olefin polymer in the presence of an olefin polymerization catalyst comprising the metallocene compounds (A). Also, the technical scope of the present invention is not limited to the following embodiments.

[Metallocene Compounds (A)]

Metallocene compounds (A) of the present invention is represented by Formula [I] below.

[Chem. 3]

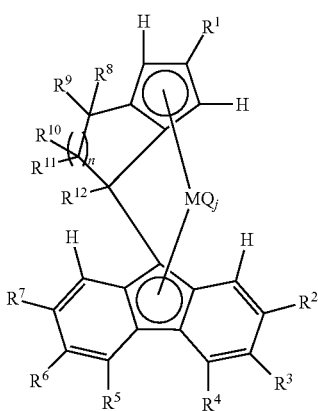

[I]

In the formula, $R^1$ is an adamantyl group derivative; $R^2$ and $R^7$ are selected from a hydrocarbon group, a silicon-containing group, and a halogen-containing hydrocarbon group; $R^3$ and $R^6$ are hydrogen atoms; $R^4$, $R^5$, $R^8$, $R^9$, $R^{10}$, $R^{11}$, and $R^{12}$ are selected from a hydrogen atom, a hydrocarbon group, a silicon-containing group, a halogen atom, and a halogen-containing hydrocarbon group and may be the same or different from each other, and adjacent substituents among $R^4$, $R^5$, $R^8$, $R^9$, $R^{10}$, $R^{11}$, and $R^{12}$ may combine to form a ring; n is an integer between 1 and 3; M is a Group 4 transition metal; Q is a halogen atom, a hydrocarbon group, an anionic Ligand, or a neutral ligand that is bondable with a lone pair and may be the same or different from each other; and j is an integer between 1 and 4.)

An olefin polymer may be efficiently produced by using an olefin polymerization catalyst comprising metallocene compound (A) of the present invention, for example, in polymerizing an α-olefin such as propylene. That is, metallocene compound (A) of the present invention may preferably used as a catalyst component for olefin polymerization in olefin polymerization to produce olefin polymers, in particular, propylene (co)polymers.

The carbon numbers of the hydrocarbon groups of $R^2$, $R^4$, $R^5$, and $R^7$ to $R^{12}$ are preferably between 1 and 40, and more preferably between 1 and 20. Examples of hydrocarbon groups include alkyl groups having 1 to 20 carbon atoms, saturated alicyclic groups having 3 to 20 carbon atoms, aryl groups having 6 to 20 carbon atoms, and aralkyl groups having 7 to 20 carbon atoms.

Examples of alkyl groups having 1 to 20 carbon atoms include linear alkyl groups such as methyl group, ethyl group, n-propyl group, n-butyl group, n-pentyl group, n-hexyl group, n-heptyl group, n-octyl group, n-nonyl group, and n-decanyl group; and branched alkyl groups such as iso-propyl group, tert-butyl group, amyl group, 3-methylpentyl group, 1,1-diethylpropyl group, 1,1-dimethylbutyl group, 1-methyl-1-propylbutyl group, 1,1-propylbutyl group, 1,1-dimethyl-2-methylpropyl group, 1-methyl-1-isopropyl-2-methylpropyl group.

Examples of saturated alicyclic groups having 3 to 20 carbon atoms include cycloalkyl groups such as cyclopentyl group, cyclohexyl group, cycloheptyl group, and cycloextyl group; and alicyclic polycyclic groups such as norbornyl group and adamantly group.

Examples of aryl groups having 6 to 20 carbon atoms include unsubstituted aryl groups such as phenyl group, naphthyl group, phenanthryl group, anthracenyl group, and biphenyl group; and alkylaryl groups such as o-tolyl group, m-tolyl group, p-tolyl group, ethylphenyl group, n-propylphenyl group, iso-propylphenyl group, n-butylphenyl group, sec-butylphenyl group, tert-bubylphenyl, and xylyl group.

Examples of aralkyl groups having 7 to 20 carbon atoms include unsubstituted aralkyl groups such as benzyl group, cumyl group, α-phenethyl group, β-phenethyl group, diphenylmethyl group, naphthylmethyl group, and neophyl group; and alkylaralkyl groups such as o-methylbenzyl group, m-methylbenzyl group, p-methylbenzyl group, ethylbenzyl group, n-propylbenzyl group, isopropylbenzyl group, n-butylbenzyl group, sec-butylbenzyl group, tert-butylbenzyl group.

Hydrocarbon groups preferably have 1 to 10 carbon atoms.

Examples of silicon-containing groups include alkylsilyl groups such as methylsilyl group, dimethylsilyl group, trimethylsilyl group, ethylsilyl group, diethylsilyl group, triethylsilyl group, and dimethyl-tert-butylsilyl group; and arylsilyl groups such as dimethylphenylsilyl group, diphenylmethylsilyl group, and triphenylsilyl group.

Examples of halogen-containing hydrocarbon groups include the groups that result from substitution of at least one hydrogen atom of the above-mentioned hydrocarbon group with a halogen group, specifically halogen-substituted alkyl groups including fluoroalkyl groups such as trifluoromethyl group; halogen-substituted aryl groups including halogen-substituted groups of the above-mentioned unsubstituted aryl groups including fluoroaryl groups such as pentafluorophenyl group, chloroaryl groups such as o-chlorophenyl group, m-chlorophenyl group, p-chlorophenyl group, and chloronaphthyl group, bromoaryl groups such as o-bromophenyl group, m-bromophenyl group, p-bromophenyl group, and bromonaphthyl group, and iodoaryl groups such as o-iodophenyl group, m-iodophenyl group, p-iodophenyl group, and iodonaphthyl group, and halogen-substituted groups of the above-mentioned alkylaryl groups including fluoroalkylaryl groups such as trifluoromethylphenyl group, bromoalkylaryl groups such as bromomethylphenyl group and dibromomethylphenyl group, and iodoalkylaryl groups such as iodomethylphenyl group and diiodomethylphenyl group; and halogen-substituted aralkyl groups including halogen-substituted groups of the above-mentioned unsubstituted aralkyl groups including chloroaralkyl groups such as o-chlorobenzyl group, m-chlorobenzyl group, p-chlorobenzyl group, and chlorophenethyl group, bromoaralkyl groups such as o-bromobenzyl group, m-bromobenzyl group, p-bromobenzyl group, and bromophenethyl group, and iodoaralkyl groups such as o-iodobenzyl group, m-iodobenzyl group, p-iodobenzyl group, and iodophenethyl group.

In Formula [I], $R^1$ is preferably 1-adamantyl group, 2-adamantyl group, 3,5-dimethyl-1-adamantyl group, or 3,5,7-trimethyl-1-adamantyl group, more preferably 1-adamantyl group, 3,5-dimethyl-1-adamantyl group, or 3,5,7-trimethyl-1-adamantyl group, and particularly preferably 1-adamantyl group, in terms of efficiently producing an olefin polymer that is formed because $R^1$ is an above-mentioned group. Due to the three-dimensional volume of $R^1$, it would probably be difficult for an anion to come close to metallocene cation derived from Formula [I] which is presumably an active species. Thus, it is assumed that (1) it is easier for a monomer to come close to a metallocene cation as the metallocene cation's configuration space widens and (2) the reactivity with olefin is increased as the Lewis acidity of metallocene cation is improved, leading to improved catalytic activity.

In Formula [I], the positions 1 and 8 of the fluorenyl are preferably hydrogen atoms in terms of efficiently producing an olefin polymer. The positions 3 and 6 of the fluorenyl are preferably hydrogen atoms in terms of the melt flowability of an olefin polymer produced.

$R^2$ and $R^7$ are preferably each independently a hydrocarbon group having 4 to 10 carbon atoms. Hydrogen groups having 4 to 10 carbon atoms are preferably isobutyl group, tert-butyl group, tert-amyl group, phenyl group, 1-methylcyclohexyl group, or 1-adamantyl groups, more preferably tert-butyl group, tert-pentyl group, 1-methylcyclohexyl group, or 1-adamantyl group, and particularly preferably tert-butyl group, in terms of efficiently producing an olefin polymer.

Examples of silicon-containing groups include alkylsilyl groups such as methylsilyl group, dimethylsilyl group, trimethylsilyl group, ethylsilyl group, diethylsilyl group, triethylsilyl group, and dimethyl-tert-butylsilyl group; and arylsilyl groups such as dimethylphenylsilyl group, diphenylmethylsilyl group, and triphenylsilyl group.

Examples of halogen atoms include fluorine atom, chlorine atom, bromine atom, and iodine atom. Examples of halogen-containing hydrocarbon groups include groups that result from substitution of at least one hydrogen atom of the abovementioned hydrocarbon group with a halogen group, specifically halogen-substituted alkyl groups including fluoroalkyl groups such as trifluoromethyl group; halogen-substituted aryl groups including halogen-substituted groups of the abovementioned unsubstituted aryl groups including fluoroaryl groups such as pentafluorophenyl group, chloroaryl groups such as o-chlorophenyl group, m-chlorophenyl group, p-chlorophenyl group, and chloronaphthyl group, bromoaryl groups such o-bromophenyl group, m-bromophenyl group, p-bromophenyl group, and bromonaphthyl group, and iodoaryl groups such as o-iodophenyl group, m-iodophenyl group, p-iodophenyl group, and iodonaphthyl group, and halogen-substituted groups of the above-mentioned alkylaryl groups including fluoroalkylaryl groups such as trifluoromethylphenyl group, bromoalkylaryl groups such as bromomethylphenyl group and dibromomethylphenyl group, and iodoalkylaryl groups such as iodomethyl phenyl group and diiodomethylphenyl group; halogen-substituted aralkyl groups including halogen-substituted groups of the above-mentioned unsubstituted aralkyl groups including chloroaralkyl groups such as m-chlorobenzyl group, m-chlorobenzyl group, p-chlorobenzyl group, and chlorophenethyl group, bromoaralkyl groups such as o-bromobenzyl group,
m-bromobenzyl group, p-bromobenzyl group, and bromophenethyl group, and iodoaralkyl groups such as o-iodobenzyl group, m-iodobenzyl group, p-iodobenzyl group, and iodophenethyl group.

In Formula [I], $R^3$ and $R^6$ are hydrogen atoms. This is preferable in terms of efficiently producing an olefin polymer that forms because $R^3$ and $R^6$ are hydrogen atoms.

In Formula [I], $R^4$ and $R^5$ are preferably each independently hydrogen atom, hydrocarbon group having 1 to 10 carbon atoms, or halogen atom, and among those, more preferably hydrogen atom, methyl group, ethyl group, chloro group, bromo group, or fluoro group, and particularly preferably hydrogen atom. This is preferable in terms of efficiently producing an olefin polymer that forms because $R^4$ and $R^5$ are one of the above groups.

In Formula [I], $R^8$, $R^9$, $R^{10}$, and $R^{11}$ are preferably each independently hydrogen atom or hydrocarbon group, and among these, more preferably hydrogen atom, methyl group, ethyl group, isopropyl group, or cyclohexyl group, and particularly preferably hydrogen atom, methyl group, or isopropyl group. Here, in a preferred embodiment of the present invention, $R^8$ and $R^9$ are hydrocarbon groups, more preferably hydrocarbon groups having 1 to 20 carbon atoms. Further, in a preferred embodiment of the present invention, $R^{10}$ and $R^{11}$ are hydrogen atoms. Also, in another preferred embodiment of the present invention, $R^9$ and $R^{10}$ are preferably groups that combine together and form a cyclopentane ring, or groups that combine together to form a cyclohexane ring, and particularly preferably groups that combine together and form a cyclohexane ring.

In Formula [I], $R^{12}$ is preferably a hydrocarbon group having 1 to 20 carbon atoms, and more preferably a hydrocarbon group having 1 to 10 carbon atoms. It is more preferably methyl group, ethyl, n-propyl, n-butyl group, or phenyl group, and particularly preferably methyl group. This is preferable in terms of efficiently producing an olefin polymer that forms because $R^{12}$ is an above-mentioned group.

<M, Q, n and j>

M is a Group 4 transition metal, that is, Ti, Zr, or Hf. It is preferably Zr or Hf and particularly preferably Zr.

Q represents a halogen atom (e.g. fluorine atom, chloride atom, bromine atom, and iodine atom), a hydrocarbon group, a neutral conjugated or nonconjugated diene having 10 or fewer carbon atoms, an anionic ligand, or a neutral ligand that is bondable with a lone pair.

The hydrocarbon group for Q is preferably alkyl group having 1 to 10 carbon atoms or cycloalkyl group having 3 to 10 carbon atoms. Examples of alkyl group having 1 to 10 carbon atoms include methyl group, ethyl group, n-propyl group, iso-propyl group, 2-methylpropyl group, 1,1-dimethylpropyl group, 2,2-dimethylpropyl group, 1,1-diethylpropyl group, 1-ethyl-1-methylpropyl group, 1,1,2,2-tetramethylpropyl group, sec-butyl group, tert-butyl group, 1,1-dimethylbutyl group, 1,1,3-trimethylbutyl group, and neopentyl group; and examples of cycloalkyl group having 3 to 10 carbon atoms include cyclohexylmethyl group, cyclohexyl group, and 1-methyl-1-cyclohexyl group. It is more preferable for the hydrocarbon group to have 5 or fewer carbon atoms.

Examples of the neutral conjugated or nonconjugated diene having 10 or fewer carbon atoms include s-cis- or s-trans-$\eta^4$-1,3-butadiene, s-cis- or s-trans-$\eta^4$-1,4-diphenyl-1,3-butadiene,
s-cis- or s-trans-$\eta^4$-3-methyl-1,3-pentadiene,
s-cis- or s-trans-$\eta^4$-1,4-dibenzyl-1,3-butadiene,
s-cis- or s-trans-$\eta^4$-2,4-hexadiene, s-cis- or s-trans-$\eta^4$-1,3-pentadiene, s-cis- or s-trans-$\eta^4$-1,4-ditolyl-1,3-butadiene, s-cis- or s-trans-$\eta^4$-bis(trimethylsilyl)-1,3-butadiene.

Examples of the anionic ligand include alkoxy groups such as methoxy and tert-butoxy; aryloxy groups such as phenoxy; carboxylate groups such as acetate and benzoate; and sulfonate groups such as mesylate and tosylate.

Examples of the neutral ligand that is bondable with a lone pair include organophosphorus compounds such as trimethylphosphine, triethylphosphine, triphenylphosphine, and diphenylmethylphosphine; and ethers such as tetrahydrofuran (THF), diethyl ether, dioxane, and 1,2-dimethoxyethane.

A preferred embodiment of Q is a halogen atom or alkyl group having 1 to 5 carbon atoms.

n is an integer between 1 and 3, preferably 1 or 2, and more preferably 1. This is preferable in terms of efficiently producing an olefin polymer that is formed because n is one of the above-mentioned integers.

j is an integer between 1 and 4, preferably 2.

Example of Metallocene Compounds (A)

Specific examples of metallocene compounds (A) of the present invention will be shown, but the scope of the invention is not limited to these examples. Further, metallocene compounds (A) in the present invention may be used singly, or two or more can be used in combination.

For convenience purposes in description, if the ligand structure except for $MQ_j$ (metal moiety) of the metallocene compound are divided into two, cyclopentadienyl derivative moiety and fluorenyl moiety, and represent fluorenyl moiety with Flu, the cyclopentadienyl derivative moiety is represented by (i) (n=1), (ii) (n=2), and (iii) (n=3) below.

[Chem. 4]

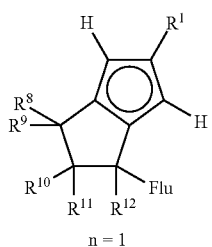

(i)

n = 1

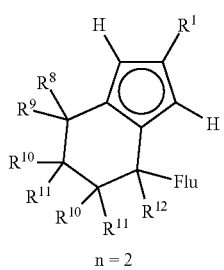

(ii)

n = 2

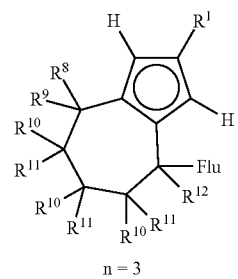

(iii)

n = 3

Examples of a structure that forms by two substituents combining together include (i-1) ($R^{11}$ and $R^{12}$ combine together and form a cyclopentane ring) and (i-2) ($R^{11}$ and $R^{12}$ combine together and form a cyclohexane ring).

[Chem. 5]

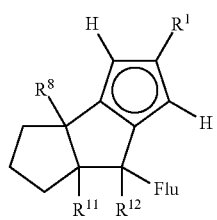

(i-1)

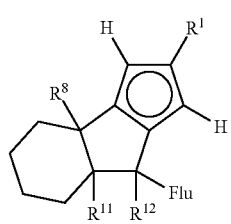

(i-2)

If the ligand structure except for $MQ_j$ (metal moiety) in the metallocene compound are divided into three, adamantyl derivative moiety ($\alpha$), cyclopentadienyl derivative moiety ($\beta$), and fluorenyl moiety ($\gamma$), and represent the adamantyl derivative moiety as Adm and cyclopentadienyl derivative moiety as Cp, specific examples of each partial structure are shown in Tables 1 through 3, and specific examples of ligand structures according to these combinations are shown in Tables 4-1 through 4-4.

TABLE 1

| | Adamantyl Derivative Moiety |
|---|---|
| α1 | 1-adamantyl |
| α2 | 2-adamantyl |
| α3 | 3,5-dimethyl-1-adamantyl |
| α4 | 3,5,7-trimethyl-1-adamantyl |

TABLE 2
| | Cyclopentadienyl Derivative Moiety |
|---|---|
| β1 | 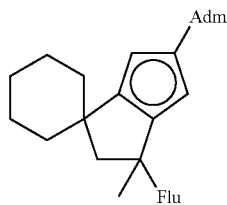 |
| β2 | 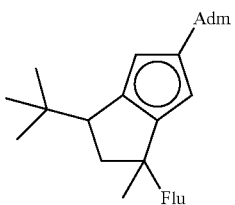 |
| β3 | 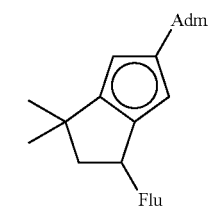 |
| β4 | 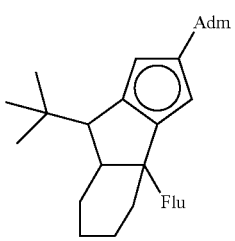 |
| β5 | 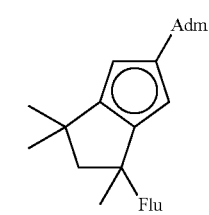 |
| β6 | 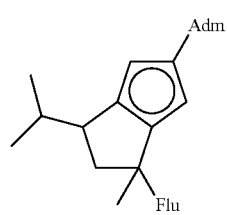 |
| β7 | 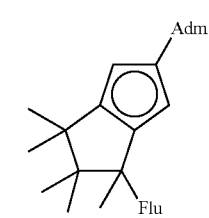 |
TABLE 2-continued
| | Cyclopentadienyl Derivative Moiety |
|---|---|
| β8 | 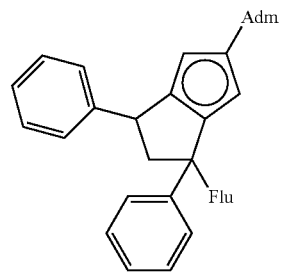 |
| β9 | 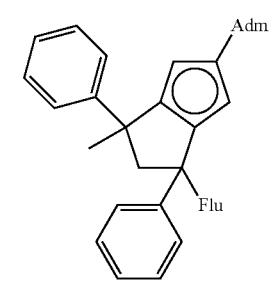 |
| β10 | 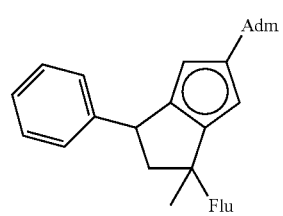 |
| β11 | 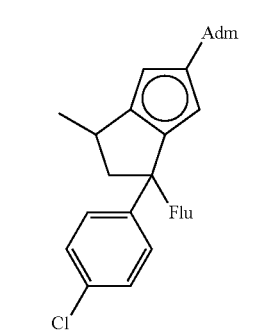 |
| β12 | 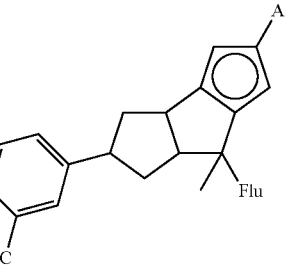 |
| β13 | 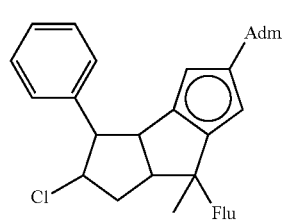 |

TABLE 2-continued
Cyclopentadienyl Derivative Moiety
β14 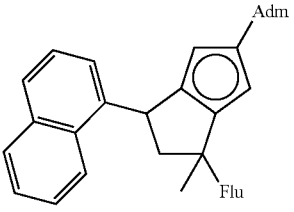
β15 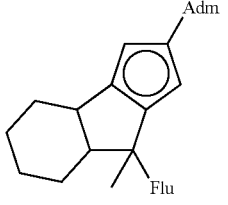
β16 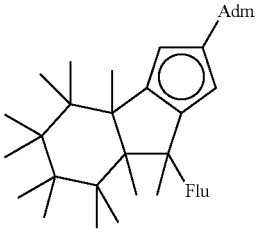
β17 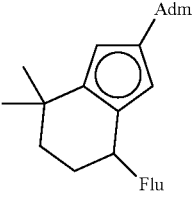
TABLE 3
Fluorenyl Moiety
γ1 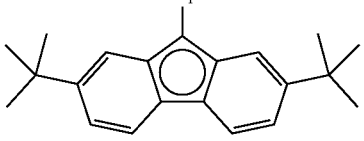
γ2 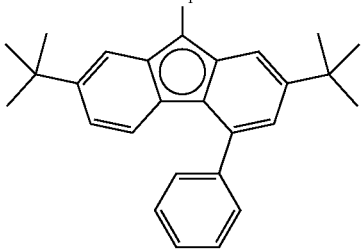
γ3 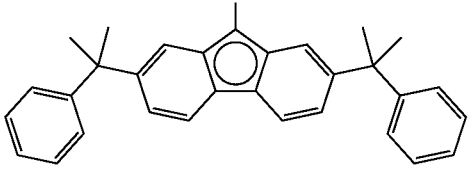
γ4 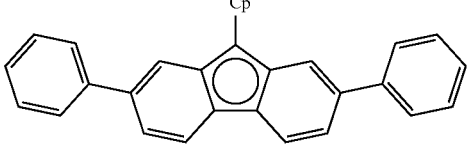
γ5 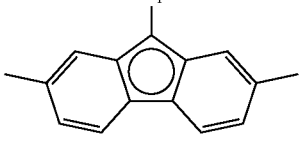
γ6 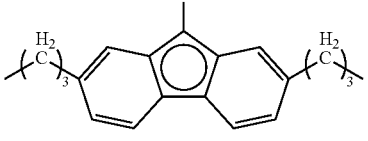
γ7 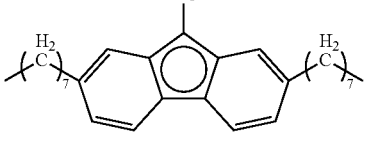
γ8 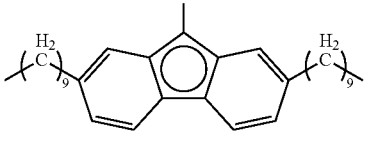
γ9 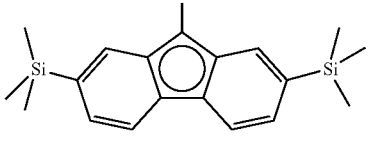
γ10 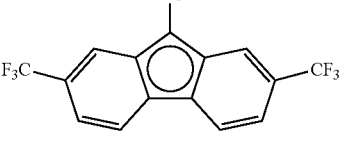
γ11 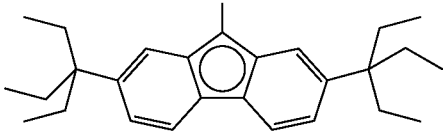

TABLE 3-continued

Fluorenyl Moiety

γ12 [structure: fluorene with Cp at 9-position and phenyl groups at 2,7-positions]

γ13 [structure: fluorene with Cp at 9-position and naphthyl groups at 2,7-positions]

TABLE 4-1

Ligand Structure 1

| No. | Adamantyl Derivative Moiety | Cyclopentadienyl Derivative Moiety | Fluorenyl Derivative Moiety |
|---|---|---|---|
| 1 | α1 | β1 | γ1 |
| 2 | α1 | β1 | γ2 |
| 3 | α1 | β1 | γ3 |
| 4 | α1 | β1 | γ4 |
| 5 | α1 | β1 | γ5 |
| 6 | α1 | β1 | γ6 |
| 7 | α1 | β1 | γ7 |
| 8 | α1 | β1 | γ8 |
| 9 | α1 | β1 | γ9 |
| 10 | α1 | β1 | γ10 |
| 11 | α1 | β1 | γ11 |
| 12 | α1 | β1 | γ12 |
| 13 | α1 | β1 | γ13 |
| 14 | α1 | β2 | γ1 |
| 15 | α1 | β2 | γ2 |
| 16 | α1 | β2 | γ3 |
| 17 | α1 | β2 | γ4 |
| 18 | α1 | β2 | γ5 |
| 19 | α1 | β2 | γ6 |
| 20 | α1 | β2 | γ7 |
| 21 | α1 | β2 | γ8 |
| 22 | α1 | β2 | γ9 |
| 23 | α1 | β2 | γ10 |
| 24 | α1 | β2 | γ11 |
| 25 | α1 | β2 | γ12 |
| 26 | α1 | β2 | γ13 |
| 27 | α1 | β3 | γ1 |
| 28 | α1 | β3 | γ2 |
| 29 | α1 | β3 | γ3 |
| 30 | α1 | β3 | γ4 |
| 31 | α1 | β3 | γ5 |
| 32 | α1 | β3 | γ6 |
| 33 | α1 | β3 | γ7 |
| 34 | α1 | β3 | γ8 |
| 35 | α1 | β3 | γ9 |
| 36 | α1 | β3 | γ10 |
| 37 | α1 | β3 | γ11 |
| 38 | α1 | β3 | γ12 |
| 39 | α1 | β3 | γ13 |
| 40 | α1 | β4 | γ1 |
| 41 | α1 | β4 | γ2 |
| 42 | α1 | β4 | γ3 |
| 43 | α1 | β4 | γ4 |
| 44 | α1 | β4 | γ5 |
| 45 | α1 | β4 | γ6 |
| 46 | α1 | β4 | γ7 |
| 47 | α1 | β4 | γ8 |
| 48 | α1 | β4 | γ9 |
| 49 | α1 | β4 | γ10 |
| 50 | α1 | β4 | γ11 |
| 51 | α1 | β4 | γ12 |
| 52 | α1 | β4 | γ13 |
| 53 | α1 | β5 | γ1 |
| 54 | α1 | β5 | γ2 |
| 55 | α1 | β5 | γ3 |
| 56 | α1 | β5 | γ4 |
| 57 | α1 | β5 | γ5 |
| 58 | α1 | β5 | γ6 |
| 59 | α1 | β5 | γ7 |
| 60 | α1 | β5 | γ8 |
| 61 | α1 | β5 | γ9 |
| 62 | α1 | β5 | γ10 |
| 63 | α1 | β5 | γ11 |
| 64 | α1 | β5 | γ12 |
| 65 | α1 | β5 | γ13 |
| 66 | α1 | β6 | γ1 |
| 67 | α1 | β6 | γ2 |
| 68 | α1 | β6 | γ3 |
| 69 | α1 | β6 | γ4 |
| 70 | α1 | β6 | γ5 |
| 71 | α1 | β6 | γ6 |
| 72 | α1 | β6 | γ7 |
| 73 | α1 | β6 | γ8 |
| 74 | α1 | β6 | γ9 |
| 75 | α1 | β6 | γ10 |
| 76 | α1 | β6 | γ11 |
| 77 | α1 | β6 | γ12 |
| 78 | α1 | β6 | γ13 |
| 79 | α1 | β7 | γ1 |
| 80 | α1 | β7 | γ2 |
| 81 | α1 | β7 | γ3 |
| 82 | α1 | β7 | γ4 |
| 83 | α1 | β7 | γ5 |
| 84 | α1 | β7 | γ6 |
| 85 | α1 | β7 | γ7 |
| 86 | α1 | β7 | γ8 |
| 87 | α1 | β7 | γ9 |
| 88 | α1 | β7 | γ10 |
| 89 | α1 | β7 | γ11 |
| 90 | α1 | β7 | γ12 |
| 91 | α1 | β7 | γ13 |
| 92 | α1 | β8 | γ1 |
| 93 | α1 | β8 | γ2 |
| 94 | α1 | β8 | γ3 |
| 95 | α1 | β8 | γ4 |
| 96 | α1 | β8 | γ5 |
| 97 | α1 | β8 | γ6 |
| 98 | α1 | β8 | γ7 |
| 99 | α1 | β8 | γ8 |
| 100 | α1 | β8 | γ9 |
| 101 | α1 | β8 | γ10 |
| 102 | α1 | β8 | γ11 |
| 103 | α1 | β8 | γ12 |
| 104 | α1 | β8 | γ13 |
| 105 | α1 | β9 | γ1 |
| 106 | α1 | β9 | γ2 |
| 107 | α1 | β9 | γ3 |
| 108 | α1 | β9 | γ4 |
| 109 | α1 | β9 | γ5 |
| 110 | α1 | β9 | γ6 |
| 111 | α1 | β9 | γ7 |
| 112 | α1 | β9 | γ8 |
| 113 | α1 | β9 | γ9 |
| 114 | α1 | β9 | γ10 |
| 115 | α1 | β9 | γ11 |
| 116 | α1 | β9 | γ12 |
| 117 | α1 | β9 | γ13 |
| 118 | α1 | β10 | γ1 |
| 119 | α1 | β10 | γ2 |
| 120 | α1 | β10 | γ3 |
| 121 | α1 | β10 | γ4 |
| 122 | α1 | β10 | γ5 |
| 123 | α1 | β10 | γ6 |
| 124 | α1 | β10 | γ7 |

TABLE 4-1-continued

Ligand Structure 1

| No. | Adamantyl Derivative Moiety | Cyclopentadienyl Derivative Moiety | Fluorenyl Derivative Moiety |
|---|---|---|---|
| 125 | α1 | β10 | γ8 |
| 126 | α1 | β10 | γ9 |
| 127 | α1 | β10 | γ10 |
| 128 | α1 | β10 | γ11 |
| 129 | α1 | β10 | γ12 |
| 130 | α1 | β10 | γ13 |
| 131 | α1 | β11 | γ1 |
| 132 | α1 | β11 | γ2 |
| 133 | α1 | β11 | γ3 |
| 134 | α1 | β11 | γ4 |
| 135 | α1 | β11 | γ5 |
| 136 | α1 | β11 | γ6 |
| 137 | α1 | β11 | γ7 |
| 138 | α1 | β11 | γ8 |
| 139 | α1 | β11 | γ9 |
| 140 | α1 | β11 | γ10 |
| 141 | α1 | β11 | γ11 |
| 142 | α1 | β11 | γ12 |
| 143 | α1 | β11 | γ13 |
| 144 | α1 | β12 | γ1 |
| 145 | α1 | β12 | γ2 |
| 146 | α1 | β12 | γ3 |
| 147 | α1 | β12 | γ4 |
| 148 | α1 | β12 | γ5 |
| 149 | α1 | β12 | γ6 |
| 150 | α1 | β12 | γ7 |
| 151 | α1 | β12 | γ8 |
| 152 | α1 | β12 | γ9 |
| 153 | α1 | β12 | γ10 |
| 154 | α1 | β12 | γ11 |
| 155 | α1 | β12 | γ12 |
| 156 | α1 | β12 | γ13 |
| 157 | α1 | β13 | γ1 |
| 158 | α1 | β13 | γ2 |
| 159 | α1 | β13 | γ3 |
| 160 | α1 | β13 | γ4 |
| 161 | α1 | β13 | γ5 |
| 162 | α1 | β13 | γ6 |
| 163 | α1 | β13 | γ7 |
| 164 | α1 | β13 | γ8 |
| 165 | α1 | β13 | γ9 |
| 166 | α1 | β13 | γ10 |
| 167 | α1 | β13 | γ11 |
| 168 | α1 | β13 | γ12 |
| 169 | α1 | β13 | γ13 |
| 170 | α1 | β14 | γ1 |
| 171 | α1 | β14 | γ2 |
| 172 | α1 | β14 | γ3 |
| 173 | α1 | β14 | γ4 |
| 174 | α1 | β14 | γ5 |
| 175 | α1 | β14 | γ6 |
| 176 | α1 | β14 | γ7 |
| 177 | α1 | β14 | γ8 |
| 178 | α1 | β14 | γ9 |
| 179 | α1 | β14 | γ10 |
| 180 | α1 | β14 | γ11 |
| 181 | α1 | β14 | γ12 |
| 182 | α1 | β14 | γ13 |
| 183 | α1 | β15 | γ1 |
| 184 | α1 | β15 | γ2 |
| 185 | α1 | β15 | γ3 |
| 186 | α1 | β15 | γ4 |
| 187 | α1 | β15 | γ5 |
| 188 | α1 | β15 | γ6 |
| 189 | α1 | β15 | γ7 |
| 190 | α1 | β15 | γ8 |
| 191 | α1 | β15 | γ9 |
| 192 | α1 | β15 | γ10 |
| 193 | α1 | β15 | γ11 |
| 194 | α1 | β15 | γ12 |
| 195 | α1 | β15 | γ13 |
| 196 | α1 | β16 | γ1 |
| 197 | α1 | β16 | γ2 |
| 198 | α1 | β16 | γ3 |
| 199 | α1 | β16 | γ4 |
| 200 | α1 | β16 | γ5 |
| 201 | α1 | β16 | γ6 |
| 202 | α1 | β16 | γ7 |
| 203 | α1 | β16 | γ8 |
| 204 | α1 | β16 | γ9 |
| 205 | α1 | β16 | γ10 |
| 206 | α1 | β16 | γ11 |
| 207 | α1 | β16 | γ12 |
| 208 | α1 | β16 | γ13 |
| 209 | α1 | β17 | γ1 |
| 210 | α1 | β17 | γ2 |
| 211 | α1 | β17 | γ3 |
| 212 | α1 | β17 | γ4 |
| 213 | α1 | β17 | γ5 |
| 214 | α1 | β17 | γ6 |
| 215 | α1 | β17 | γ7 |
| 216 | α1 | β17 | γ8 |
| 217 | α1 | β17 | γ9 |
| 218 | α1 | β17 | γ10 |
| 219 | α1 | β17 | γ11 |
| 220 | α1 | β17 | γ12 |
| 221 | α1 | β17 | γ13 |
| 222 | α2 | β1 | γ1 |
| 223 | α2 | β1 | γ2 |
| 224 | α2 | β1 | γ3 |
| 225 | α2 | β1 | γ4 |
| 226 | α2 | β1 | γ5 |
| 227 | α2 | β1 | γ6 |
| 228 | α2 | β1 | γ7 |
| 229 | α2 | β1 | γ8 |
| 230 | α2 | β1 | γ9 |
| 231 | α2 | β1 | γ10 |
| 232 | α2 | β1 | γ11 |
| 233 | α2 | β1 | γ12 |
| 234 | α2 | β1 | γ13 |
| 235 | α2 | β2 | γ1 |
| 236 | α2 | β2 | γ2 |
| 237 | α2 | β2 | γ3 |
| 238 | α2 | β2 | γ4 |
| 239 | α2 | β2 | γ5 |
| 240 | α2 | β2 | γ6 |

TABLE 4-2

Ligand Structure (Continuation)

| No. | Adamantyl Derivative Moiety | Cyclopentadienyl Derivative Moiety | Fluorenyl Derivative Moiety |
|---|---|---|---|
| 241 | α2 | β2 | γ7 |
| 242 | α2 | β2 | γ8 |
| 243 | α2 | β2 | γ9 |
| 244 | α2 | β2 | γ10 |
| 245 | α2 | β2 | γ11 |
| 246 | α2 | β2 | γ12 |
| 247 | α2 | β2 | γ13 |
| 248 | α2 | β3 | γ1 |
| 249 | α2 | β3 | γ2 |
| 250 | α2 | β3 | γ3 |
| 251 | α2 | β3 | γ4 |
| 252 | α2 | β3 | γ5 |
| 253 | α2 | β3 | γ6 |
| 254 | α2 | β3 | γ7 |
| 255 | α2 | β3 | γ8 |
| 256 | α2 | β3 | γ9 |
| 257 | α2 | β3 | γ10 |
| 258 | α2 | β3 | γ11 |
| 259 | α2 | β3 | γ12 |
| 260 | α2 | β3 | γ13 |

TABLE 4-2-continued

Ligand Structure (Continuation)

| No. | Adamantyl Derivative Moiety | Cyclopentadienyl Derivative Moiety | Fluorenyl Derivative Moiety |
|---|---|---|---|
| 261 | α2 | β4 | γ1 |
| 262 | α2 | β4 | γ2 |
| 263 | α2 | β4 | γ3 |
| 264 | α2 | β4 | γ4 |
| 265 | α2 | β4 | γ5 |
| 266 | α2 | β4 | γ6 |
| 267 | α2 | β4 | γ7 |
| 268 | α2 | β4 | γ8 |
| 269 | α2 | β4 | γ9 |
| 270 | α2 | β4 | γ10 |
| 271 | α2 | β4 | γ11 |
| 272 | α2 | β4 | γ12 |
| 273 | α2 | β4 | γ13 |
| 274 | α2 | β5 | γ1 |
| 275 | α2 | β5 | γ2 |
| 276 | α2 | β5 | γ3 |
| 277 | α2 | β5 | γ4 |
| 278 | α2 | β5 | γ5 |
| 279 | α2 | β5 | γ6 |
| 280 | α2 | β5 | γ7 |
| 281 | α2 | β5 | γ8 |
| 282 | α2 | β5 | γ9 |
| 283 | α2 | β5 | γ10 |
| 284 | α2 | β5 | γ11 |
| 285 | α2 | β5 | γ12 |
| 286 | α2 | β5 | γ13 |
| 287 | α2 | β6 | γ1 |
| 288 | α2 | β6 | γ2 |
| 289 | α2 | β6 | γ3 |
| 290 | α2 | β6 | γ4 |
| 291 | α2 | β6 | γ5 |
| 292 | α2 | β6 | γ6 |
| 293 | α2 | β6 | γ7 |
| 294 | α2 | β6 | γ8 |
| 295 | α2 | β6 | γ9 |
| 296 | α2 | β6 | γ10 |
| 297 | α2 | β6 | γ11 |
| 298 | α2 | β6 | γ12 |
| 299 | α2 | β6 | γ13 |
| 300 | α2 | β7 | γ1 |
| 301 | α2 | β7 | γ2 |
| 302 | α2 | β7 | γ3 |
| 303 | α2 | β7 | γ4 |
| 304 | α2 | β7 | γ5 |
| 305 | α2 | β7 | γ6 |
| 306 | α2 | β7 | γ7 |
| 307 | α2 | β7 | γ8 |
| 308 | α2 | β7 | γ9 |
| 309 | α2 | β7 | γ10 |
| 310 | α2 | β7 | γ11 |
| 311 | α2 | β7 | γ12 |
| 312 | α2 | β7 | γ13 |
| 313 | α2 | β8 | γ1 |
| 314 | α2 | β8 | γ2 |
| 315 | α2 | β8 | γ3 |
| 316 | α2 | β8 | γ4 |
| 317 | α2 | β8 | γ5 |
| 318 | α2 | β8 | γ6 |
| 319 | α2 | β8 | γ7 |
| 320 | α2 | β8 | γ8 |
| 321 | α2 | β8 | γ9 |
| 322 | α2 | β8 | γ10 |
| 323 | α2 | β8 | γ11 |
| 324 | α2 | β8 | γ12 |
| 325 | α2 | β8 | γ13 |
| 326 | α2 | β9 | γ1 |
| 327 | α2 | β9 | γ2 |
| 328 | α2 | β9 | γ3 |
| 329 | α2 | β9 | γ4 |
| 330 | α2 | β9 | γ5 |
| 331 | α2 | β9 | γ6 |
| 332 | α2 | β9 | γ7 |
| 333 | α2 | β9 | γ8 |
| 334 | α2 | β9 | γ9 |
| 335 | α2 | β9 | γ10 |
| 336 | α2 | β9 | γ11 |
| 337 | α2 | β9 | γ12 |
| 338 | α2 | β9 | γ13 |
| 339 | α2 | β10 | γ1 |
| 340 | α2 | β10 | γ2 |
| 341 | α2 | β10 | γ3 |
| 342 | α2 | β10 | γ4 |
| 343 | α2 | β10 | γ5 |
| 344 | α2 | β10 | γ6 |
| 345 | α2 | β10 | γ7 |
| 346 | α2 | β10 | γ8 |
| 347 | α2 | β10 | γ9 |
| 348 | α2 | β10 | γ10 |
| 349 | α2 | β10 | γ11 |
| 350 | α2 | β10 | γ12 |
| 351 | α2 | β10 | γ13 |
| 352 | α2 | β11 | γ1 |
| 353 | α2 | β11 | γ2 |
| 354 | α2 | β11 | γ3 |
| 355 | α2 | β11 | γ4 |
| 356 | α2 | β11 | γ5 |
| 357 | α2 | β11 | γ6 |
| 358 | α2 | β11 | γ7 |
| 359 | α2 | β11 | γ8 |
| 360 | α2 | β11 | γ9 |
| 361 | α2 | β11 | γ10 |
| 362 | α2 | β11 | γ11 |
| 363 | α2 | β11 | γ12 |
| 364 | α2 | β11 | γ13 |
| 365 | α2 | β12 | γ1 |
| 366 | α2 | β12 | γ2 |
| 367 | α2 | β12 | γ3 |
| 368 | α2 | β12 | γ4 |
| 369 | α2 | β12 | γ5 |
| 370 | α2 | β12 | γ6 |
| 371 | α2 | β12 | γ7 |
| 372 | α2 | β12 | γ8 |
| 373 | α2 | β12 | γ9 |
| 374 | α2 | β12 | γ10 |
| 375 | α2 | β12 | γ11 |
| 376 | α2 | β12 | γ12 |
| 377 | α2 | β12 | γ13 |
| 378 | α2 | β13 | γ1 |
| 379 | α2 | β13 | γ2 |
| 380 | α2 | β13 | γ3 |
| 381 | α2 | β13 | γ4 |
| 382 | α2 | β13 | γ5 |
| 383 | α2 | β13 | γ6 |
| 384 | α2 | β13 | γ7 |
| 385 | α2 | β13 | γ8 |
| 386 | α2 | β13 | γ9 |
| 387 | α2 | β13 | γ10 |
| 388 | α2 | β13 | γ11 |
| 389 | α2 | β13 | γ12 |
| 390 | α2 | β13 | γ13 |
| 391 | α2 | β14 | γ1 |
| 392 | α2 | β14 | γ2 |
| 393 | α2 | β14 | γ3 |
| 394 | α2 | β14 | γ4 |
| 395 | α2 | β14 | γ5 |
| 396 | α2 | β14 | γ6 |
| 397 | α2 | β14 | γ7 |
| 398 | α2 | β14 | γ8 |
| 399 | α2 | β14 | γ9 |
| 400 | α2 | β14 | γ10 |
| 401 | α2 | β14 | γ11 |
| 402 | α2 | β14 | γ12 |
| 403 | α2 | β14 | γ13 |
| 404 | α2 | β15 | γ1 |
| 405 | α2 | β15 | γ2 |
| 406 | α2 | β15 | γ3 |
| 407 | α2 | β15 | γ4 |
| 408 | α2 | β15 | γ5 |

TABLE 4-2-continued

Ligand Structure (Continuation)

| No. | Adamantyl Derivative Moiety | Cyclopentadienyl Derivative Moiety | Fluorenyl Derivative Moiety |
|---|---|---|---|
| 409 | α2 | β15 | γ6 |
| 410 | α2 | β15 | γ7 |
| 411 | α2 | β15 | γ8 |
| 412 | α2 | β15 | γ9 |
| 413 | α2 | β15 | γ10 |
| 414 | α2 | β15 | γ11 |
| 415 | α2 | β15 | γ12 |
| 416 | α2 | β15 | γ13 |
| 417 | α2 | β16 | γ1 |
| 418 | α2 | β16 | γ2 |
| 419 | α2 | β16 | γ3 |
| 420 | α2 | β16 | γ4 |
| 421 | α2 | β16 | γ5 |
| 422 | α2 | β16 | γ6 |
| 423 | α2 | β16 | γ7 |
| 424 | α2 | β16 | γ8 |
| 425 | α2 | β16 | γ9 |
| 426 | α2 | β16 | γ10 |
| 427 | α2 | β16 | γ11 |
| 428 | α2 | β16 | γ12 |
| 429 | α2 | β16 | γ13 |
| 430 | α2 | β17 | γ1 |
| 431 | α2 | β17 | γ2 |
| 432 | α2 | β17 | γ3 |
| 433 | α2 | β17 | γ4 |
| 434 | α2 | β17 | γ5 |
| 435 | α2 | β17 | γ6 |
| 436 | α2 | β17 | γ7 |
| 437 | α2 | β17 | γ8 |
| 438 | α2 | β17 | γ9 |
| 439 | α2 | β17 | γ10 |
| 440 | α2 | β17 | γ11 |
| 441 | α2 | β17 | γ12 |
| 442 | α2 | β17 | γ13 |
| 443 | α3 | β1 | γ1 |
| 444 | α3 | β1 | γ2 |
| 445 | α3 | β1 | γ3 |
| 446 | α3 | β1 | γ4 |
| 447 | α3 | β1 | γ5 |
| 448 | α3 | β1 | γ6 |
| 449 | α3 | β1 | γ7 |
| 450 | α3 | β1 | γ8 |
| 451 | α3 | β1 | γ9 |
| 452 | α3 | β1 | γ10 |
| 453 | α3 | β1 | γ11 |
| 454 | α3 | β1 | γ12 |
| 455 | α3 | β1 | γ13 |
| 456 | α3 | β2 | γ1 |
| 457 | α3 | β2 | γ2 |
| 458 | α3 | β2 | γ3 |
| 459 | α3 | β2 | γ4 |
| 460 | α3 | β2 | γ5 |
| 461 | α3 | β2 | γ6 |
| 462 | α3 | β2 | γ7 |
| 463 | α3 | β2 | γ8 |
| 464 | α3 | β2 | γ9 |
| 465 | α3 | β2 | γ10 |
| 466 | α3 | β2 | γ11 |
| 467 | α3 | β2 | γ12 |
| 468 | α3 | β2 | γ13 |
| 469 | α3 | β3 | γ1 |
| 470 | α3 | β3 | γ2 |
| 471 | α3 | β3 | γ3 |
| 472 | α3 | β3 | γ4 |
| 473 | α3 | β3 | γ5 |
| 474 | α3 | β3 | γ6 |
| 475 | α3 | β3 | γ7 |
| 476 | α3 | β3 | γ8 |
| 477 | α3 | β3 | γ9 |
| 478 | α3 | β3 | γ10 |
| 479 | α3 | β3 | γ11 |
| 480 | α3 | β3 | γ12 |

TABLE 4-3

Ligand Structure (Continuation)

| No. | Adamantyl Derivative Moiety | Cyclopentadienyl Derivative Moiety | Fluorenyl Derivative Moiety |
|---|---|---|---|
| 481 | α3 | β3 | γ13 |
| 482 | α3 | β4 | γ1 |
| 483 | α3 | β4 | γ2 |
| 484 | α3 | β4 | γ3 |
| 485 | α3 | β4 | γ4 |
| 486 | α3 | β4 | γ5 |
| 487 | α3 | β4 | γ6 |
| 488 | α3 | β4 | γ7 |
| 489 | α3 | β4 | γ8 |
| 490 | α3 | β4 | γ9 |
| 491 | α3 | β4 | γ10 |
| 492 | α3 | β4 | γ11 |
| 493 | α3 | β4 | γ12 |
| 494 | α3 | β4 | γ13 |
| 495 | α3 | β5 | γ1 |
| 496 | α3 | β5 | γ2 |
| 497 | α3 | β5 | γ3 |
| 498 | α3 | β5 | γ4 |
| 499 | α3 | β5 | γ5 |
| 500 | α3 | β5 | γ6 |
| 501 | α3 | β5 | γ7 |
| 502 | α3 | β5 | γ8 |
| 503 | α3 | β5 | γ9 |
| 504 | α3 | β5 | γ10 |
| 505 | α3 | β5 | γ11 |
| 506 | α3 | β5 | γ12 |
| 507 | α3 | β5 | γ13 |
| 508 | α3 | β6 | γ1 |
| 509 | α3 | β6 | γ2 |
| 510 | α3 | β6 | γ3 |
| 511 | α3 | β6 | γ4 |
| 512 | α3 | β6 | γ5 |
| 513 | α3 | β6 | γ6 |
| 514 | α3 | β6 | γ7 |
| 515 | α3 | β6 | γ8 |
| 516 | α3 | β6 | γ9 |
| 517 | α3 | β6 | γ10 |
| 518 | α3 | β6 | γ11 |
| 519 | α3 | β6 | γ12 |
| 520 | α3 | β6 | γ13 |
| 521 | α3 | β7 | γ1 |
| 522 | α3 | β7 | γ2 |
| 523 | α3 | β7 | γ3 |
| 524 | α3 | β7 | γ4 |
| 525 | α3 | β7 | γ5 |
| 526 | α3 | β7 | γ6 |
| 527 | α3 | β7 | γ7 |
| 528 | α3 | β7 | γ8 |
| 529 | α3 | β7 | γ9 |
| 530 | α3 | β7 | γ10 |
| 531 | α3 | β7 | γ11 |
| 532 | α3 | β7 | γ12 |
| 533 | α3 | β7 | γ13 |
| 534 | α3 | β8 | γ1 |
| 535 | α3 | β8 | γ2 |
| 536 | α3 | β8 | γ3 |
| 537 | α3 | β8 | γ4 |
| 538 | α3 | β8 | γ5 |
| 539 | α3 | β8 | γ6 |
| 540 | α3 | β8 | γ7 |
| 541 | α3 | β8 | γ8 |
| 542 | α3 | β8 | γ9 |
| 543 | α3 | β8 | γ10 |
| 544 | α3 | β8 | γ11 |
| 545 | α3 | β8 | γ12 |
| 546 | α3 | β8 | γ13 |
| 547 | α3 | β9 | γ1 |
| 548 | α3 | β9 | γ2 |
| 549 | α3 | β9 | γ3 |
| 550 | α3 | β9 | γ4 |
| 551 | α3 | β9 | γ5 |
| 552 | α3 | β9 | γ6 |
| 553 | α3 | β9 | γ7 |
| 554 | α3 | β9 | γ8 |

TABLE 4-3-continued

Ligand Structure (Continuation)

| No. | Adamantyl Derivative Moiety | Cyclopentadienyl Derivative Moiety | Fluorenyl Derivative Moiety |
|---|---|---|---|
| 555 | α3 | β9 | γ9 |
| 556 | α3 | β9 | γ10 |
| 557 | α3 | β9 | γ11 |
| 558 | α3 | β9 | γ12 |
| 559 | α3 | β9 | γ13 |
| 560 | α3 | β10 | γ1 |
| 561 | α3 | β10 | γ2 |
| 562 | α3 | β10 | γ3 |
| 563 | α3 | β10 | γ4 |
| 564 | α3 | β10 | γ5 |
| 565 | α3 | β10 | γ6 |
| 566 | α3 | β10 | γ7 |
| 567 | α3 | β10 | γ8 |
| 568 | α3 | β10 | γ9 |
| 569 | α3 | β10 | γ10 |
| 570 | α3 | β10 | γ11 |
| 571 | α3 | β10 | γ12 |
| 572 | α3 | β10 | γ13 |
| 573 | α3 | β11 | γ1 |
| 574 | α3 | β11 | γ2 |
| 575 | α3 | β11 | γ3 |
| 576 | α3 | β11 | γ4 |
| 577 | α3 | β11 | γ5 |
| 578 | α3 | β11 | γ6 |
| 579 | α3 | β11 | γ7 |
| 580 | α3 | β11 | γ8 |
| 581 | α3 | β11 | γ9 |
| 582 | α3 | β11 | γ10 |
| 583 | α3 | β11 | γ11 |
| 584 | α3 | β11 | γ12 |
| 585 | α3 | β11 | γ13 |
| 586 | α3 | β12 | γ1 |
| 587 | α3 | β12 | γ2 |
| 588 | α3 | β12 | γ3 |
| 589 | α3 | β12 | γ4 |
| 590 | α3 | β12 | γ5 |
| 591 | α3 | β12 | γ6 |
| 592 | α3 | β12 | γ7 |
| 593 | α3 | β12 | γ8 |
| 594 | α3 | β12 | γ9 |
| 595 | α3 | β12 | γ10 |
| 596 | α3 | β12 | γ11 |
| 597 | α3 | β12 | γ12 |
| 598 | α3 | β12 | γ13 |
| 599 | α3 | β13 | γ1 |
| 600 | α3 | β13 | γ2 |
| 601 | α3 | β13 | γ3 |
| 602 | α3 | β13 | γ4 |
| 603 | α3 | β13 | γ5 |
| 604 | α3 | β13 | γ6 |
| 605 | α3 | β13 | γ7 |
| 606 | α3 | β13 | γ8 |
| 607 | α3 | β13 | γ9 |
| 608 | α3 | β13 | γ10 |
| 609 | α3 | β13 | γ11 |
| 610 | α3 | β13 | γ12 |
| 611 | α3 | β13 | γ13 |
| 612 | α3 | β14 | γ1 |
| 613 | α3 | β14 | γ2 |
| 614 | α3 | β14 | γ3 |
| 615 | α3 | β14 | γ4 |
| 616 | α3 | β14 | γ5 |
| 617 | α3 | β14 | γ6 |
| 618 | α3 | β14 | γ7 |
| 619 | α3 | β14 | γ8 |
| 620 | α3 | β14 | γ9 |
| 621 | α3 | β14 | γ10 |
| 622 | α3 | β14 | γ11 |
| 623 | α3 | β14 | γ12 |
| 624 | α3 | β14 | γ13 |
| 625 | α3 | β15 | γ1 |
| 626 | α3 | β15 | γ2 |
| 627 | α3 | β15 | γ3 |
| 628 | α3 | β15 | γ4 |
| 629 | α3 | β15 | γ5 |
| 630 | α3 | β15 | γ6 |
| 631 | α3 | β15 | γ7 |
| 632 | α3 | β15 | γ8 |
| 633 | α3 | β15 | γ9 |
| 634 | α3 | β15 | γ10 |
| 635 | α3 | β15 | γ11 |
| 636 | α3 | β15 | γ12 |
| 637 | α3 | β15 | γ13 |
| 638 | α3 | β16 | γ1 |
| 639 | α3 | β16 | γ2 |
| 640 | α3 | β16 | γ3 |
| 641 | α3 | β16 | γ4 |
| 642 | α3 | β16 | γ5 |
| 643 | α3 | β16 | γ6 |
| 644 | α3 | β16 | γ7 |
| 645 | α3 | β16 | γ8 |
| 646 | α3 | β16 | γ9 |
| 647 | α3 | β16 | γ10 |
| 648 | α3 | β16 | γ11 |
| 649 | α3 | β16 | γ12 |
| 650 | α3 | β16 | γ13 |
| 651 | α3 | β17 | γ1 |
| 652 | α3 | β17 | γ2 |
| 653 | α3 | β17 | γ3 |
| 654 | α3 | β17 | γ4 |
| 655 | α3 | β17 | γ5 |
| 656 | α3 | β17 | γ6 |
| 657 | α3 | β17 | γ7 |
| 658 | α3 | β17 | γ8 |
| 659 | α3 | β17 | γ9 |
| 660 | α3 | β17 | γ10 |
| 661 | α3 | β17 | γ11 |
| 662 | α3 | β17 | γ12 |
| 663 | α3 | β17 | γ13 |
| 664 | α4 | β1 | γ1 |
| 665 | α4 | β1 | γ2 |
| 666 | α4 | β1 | γ3 |
| 667 | α4 | β1 | γ4 |
| 668 | α4 | β1 | γ5 |
| 669 | α4 | β1 | γ6 |
| 670 | α4 | β1 | γ7 |
| 671 | α4 | β1 | γ8 |
| 672 | α4 | β1 | γ9 |
| 673 | α4 | β1 | γ10 |
| 674 | α4 | β1 | γ11 |
| 675 | α4 | β1 | γ12 |
| 676 | α4 | β1 | γ13 |
| 677 | α4 | β2 | γ1 |
| 678 | α4 | β2 | γ2 |
| 679 | α4 | β2 | γ3 |
| 680 | α4 | β2 | γ4 |
| 681 | α4 | β2 | γ5 |
| 682 | α4 | β2 | γ6 |
| 683 | α4 | β2 | γ7 |
| 684 | α4 | β2 | γ8 |
| 685 | α4 | β2 | γ9 |
| 686 | α4 | β2 | γ10 |
| 687 | α4 | β2 | γ11 |
| 688 | α4 | β2 | γ12 |
| 689 | α4 | β2 | γ13 |
| 690 | α4 | β3 | γ1 |
| 691 | α4 | β3 | γ2 |
| 692 | α4 | β3 | γ3 |
| 693 | α4 | β3 | γ4 |
| 694 | α4 | β3 | γ5 |
| 695 | α4 | β3 | γ6 |
| 696 | α4 | β3 | γ7 |
| 697 | α4 | β3 | γ8 |
| 698 | α4 | β3 | γ9 |
| 699 | α4 | β3 | γ10 |
| 700 | α4 | β3 | γ11 |
| 701 | α4 | β3 | γ12 |
| 702 | α4 | β3 | γ13 |

TABLE 4-3-continued

Ligand Structure (Continuation)

| No. | Adamantyl Derivative Moiety | Cyclopentadienyl Derivative Moiety | Fluorenyl Derivative Moiety |
|---|---|---|---|
| 703 | α4 | β4 | γ1 |
| 704 | α4 | β4 | γ2 |
| 705 | α4 | β4 | γ3 |
| 706 | α4 | β4 | γ4 |
| 707 | α4 | β4 | γ5 |
| 708 | α4 | β4 | γ6 |
| 709 | α4 | β4 | γ7 |
| 710 | α4 | β4 | γ8 |
| 711 | α4 | β4 | γ9 |
| 712 | α4 | β4 | γ10 |
| 713 | α4 | β4 | γ11 |
| 714 | α4 | β4 | γ12 |
| 715 | α4 | β4 | γ13 |
| 716 | α4 | β5 | γ1 |
| 717 | α4 | β5 | γ2 |
| 718 | α4 | β5 | γ3 |
| 719 | α4 | β5 | γ4 |
| 720 | α4 | β5 | γ5 |

TABLE 4-4

Ligand Structure (Continuation)

| No. | Adamantyl Derivative Moiety | Cyclopentadienyl Derivative Moiety | Fluorenyl Derivative Moiety |
|---|---|---|---|
| 721 | α4 | β5 | γ6 |
| 722 | α4 | β5 | γ7 |
| 723 | α4 | β5 | γ8 |
| 724 | α4 | β5 | γ9 |
| 725 | α4 | β5 | γ10 |
| 726 | α4 | β5 | γ11 |
| 727 | α4 | β5 | γ12 |
| 728 | α4 | β5 | γ13 |
| 729 | α4 | β6 | γ1 |
| 730 | α4 | β6 | γ2 |
| 731 | α4 | β6 | γ3 |
| 732 | α4 | β6 | γ4 |
| 733 | α4 | β6 | γ5 |
| 734 | α4 | β6 | γ6 |
| 735 | α4 | β6 | γ7 |
| 736 | α4 | β6 | γ8 |
| 737 | α4 | β6 | γ9 |
| 738 | α4 | β6 | γ10 |
| 739 | α4 | β6 | γ11 |
| 740 | α4 | β6 | γ12 |
| 741 | α4 | β6 | γ13 |
| 742 | α4 | β7 | γ1 |
| 743 | α4 | β7 | γ2 |
| 744 | α4 | β7 | γ3 |
| 745 | α4 | β7 | γ4 |
| 746 | α4 | β7 | γ5 |
| 747 | α4 | β7 | γ6 |
| 748 | α4 | β7 | γ7 |
| 749 | α4 | β7 | γ8 |
| 750 | α4 | β7 | γ9 |
| 751 | α4 | β7 | γ10 |
| 752 | α4 | β7 | γ11 |
| 753 | α4 | β7 | γ12 |
| 754 | α4 | β7 | γ13 |
| 755 | α4 | β8 | γ1 |
| 756 | α4 | β8 | γ2 |
| 757 | α4 | β8 | γ3 |
| 758 | α4 | β8 | γ4 |
| 759 | α4 | β8 | γ5 |
| 760 | α4 | β8 | γ6 |
| 761 | α4 | β8 | γ7 |
| 762 | α4 | β8 | γ8 |
| 763 | α4 | β8 | γ9 |
| 764 | α4 | β8 | γ10 |

TABLE 4-4-continued

Ligand Structure (Continuation)

| No. | Adamantyl Derivative Moiety | Cyclopentadienyl Derivative Moiety | Fluorenyl Derivative Moiety |
|---|---|---|---|
| 765 | α4 | β8 | γ11 |
| 766 | α4 | β8 | γ12 |
| 767 | α4 | β8 | γ13 |
| 768 | α4 | β9 | γ1 |
| 769 | α4 | β9 | γ2 |
| 770 | α4 | β9 | γ3 |
| 771 | α4 | β9 | γ4 |
| 772 | α4 | β9 | γ5 |
| 773 | α4 | β9 | γ6 |
| 774 | α4 | β9 | γ7 |
| 775 | α4 | β9 | γ8 |
| 776 | α4 | β9 | γ9 |
| 777 | α4 | β9 | γ10 |
| 778 | α4 | β9 | γ11 |
| 779 | α4 | β9 | γ12 |
| 780 | α4 | β9 | γ13 |
| 781 | α4 | β10 | γ1 |
| 782 | α4 | β10 | γ2 |
| 783 | α4 | β10 | γ3 |
| 784 | α4 | β10 | γ4 |
| 785 | α4 | β10 | γ5 |
| 786 | α4 | β10 | γ6 |
| 787 | α4 | β10 | γ7 |
| 788 | α4 | β10 | γ8 |
| 789 | α4 | β10 | γ9 |
| 790 | α4 | β10 | γ10 |
| 791 | α4 | β10 | γ11 |
| 792 | α4 | β10 | γ12 |
| 793 | α4 | β10 | γ13 |
| 794 | α4 | β11 | γ1 |
| 795 | α4 | β11 | γ2 |
| 796 | α4 | β11 | γ3 |
| 797 | α4 | β11 | γ4 |
| 798 | α4 | β11 | γ5 |
| 799 | α4 | β11 | γ6 |
| 800 | α4 | β11 | γ7 |
| 801 | α4 | β11 | γ8 |
| 802 | α4 | β11 | γ9 |
| 803 | α4 | β11 | γ10 |
| 804 | α4 | β11 | γ11 |
| 805 | α4 | β11 | γ12 |
| 806 | α4 | β11 | γ13 |
| 807 | α4 | β12 | γ1 |
| 808 | α4 | β12 | γ2 |
| 809 | α4 | β12 | γ3 |
| 810 | α4 | β12 | γ4 |
| 811 | α4 | β12 | γ5 |
| 812 | α4 | β12 | γ6 |
| 813 | α4 | β12 | γ7 |
| 814 | α4 | β12 | γ8 |
| 815 | α4 | β12 | γ9 |
| 816 | α4 | β12 | γ10 |
| 817 | α4 | β12 | γ11 |
| 818 | α4 | β12 | γ12 |
| 819 | α4 | β12 | γ13 |
| 820 | α4 | β13 | γ1 |
| 821 | α4 | β13 | γ2 |
| 822 | α4 | β13 | γ3 |
| 823 | α4 | β13 | γ4 |
| 824 | α4 | β13 | γ5 |
| 825 | α4 | β13 | γ6 |
| 826 | α4 | β13 | γ7 |
| 827 | α4 | β13 | γ8 |
| 828 | α4 | β13 | γ9 |
| 829 | α4 | β13 | γ10 |
| 830 | α4 | β13 | γ11 |
| 831 | α4 | β13 | γ12 |
| 832 | α4 | β13 | γ13 |
| 833 | α4 | β14 | γ1 |
| 834 | α4 | β14 | γ2 |
| 835 | α4 | β14 | γ3 |
| 836 | α4 | β14 | γ4 |
| 837 | α4 | β14 | γ5 |
| 838 | α4 | β14 | γ6 |

TABLE 4-4-continued

Ligand Structure (Continuation)

| No. | Adamantyl Derivative Moiety | Cyclopentadienyl Derivative Moiety | Fluorenyl Derivative Moiety |
|---|---|---|---|
| 839 | α4 | β14 | γ7 |
| 840 | α4 | β14 | γ8 |
| 841 | α4 | β14 | γ9 |
| 842 | α4 | β14 | γ10 |
| 843 | α4 | β14 | γ11 |
| 844 | α4 | β14 | γ12 |
| 845 | α4 | β14 | γ13 |
| 846 | α4 | β15 | γ1 |
| 847 | α4 | β15 | γ2 |
| 848 | α4 | β15 | γ3 |
| 849 | α4 | β15 | γ4 |
| 850 | α4 | β15 | γ5 |
| 851 | α4 | β15 | γ6 |
| 852 | α4 | β15 | γ7 |
| 853 | α4 | β15 | γ8 |
| 854 | α4 | β15 | γ9 |
| 855 | α4 | β15 | γ10 |
| 856 | α4 | β15 | γ11 |
| 857 | α4 | β15 | γ12 |
| 858 | α4 | β15 | γ13 |
| 859 | α4 | β15 | γ1 |
| 860 | α4 | β16 | γ2 |
| 861 | α4 | β16 | γ3 |
| 862 | α4 | β16 | γ4 |
| 863 | α4 | β16 | γ5 |
| 864 | α4 | β16 | γ6 |
| 865 | α4 | β16 | γ7 |
| 866 | α4 | β16 | γ8 |
| 867 | α4 | β16 | γ9 |
| 868 | α4 | β16 | γ10 |
| 869 | α4 | β16 | γ11 |
| 870 | α4 | β16 | γ12 |
| 871 | α4 | β16 | γ13 |
| 872 | α4 | β17 | γ1 |
| 873 | α4 | β17 | γ2 |
| 874 | α4 | β17 | γ3 |
| 875 | α4 | β17 | γ4 |
| 876 | α4 | β17 | γ5 |
| 877 | α4 | β17 | γ6 |
| 878 | α4 | β17 | γ7 |
| 879 | α4 | β17 | γ8 |
| 880 | α4 | β17 | γ9 |
| 881 | α4 | β17 | γ10 |
| 882 | α4 | β17 | γ11 |
| 883 | α4 | β17 | γ12 |
| 884 | α4 | β17 | γ13 |

In the table above, the ligand structure in No. 53 refers to the combination of α1, β5, and γ1, the ligand structure in No. 66 refers to the combination of α1, β6, and γ1, the ligand structure in No. 183 refers to the combination of α1, β15, and γ1, and when MQ$_j$ in the metal moiety is ZrCl$_2$, they are each an example of the metallocene compounds below.

[Chem. 6]

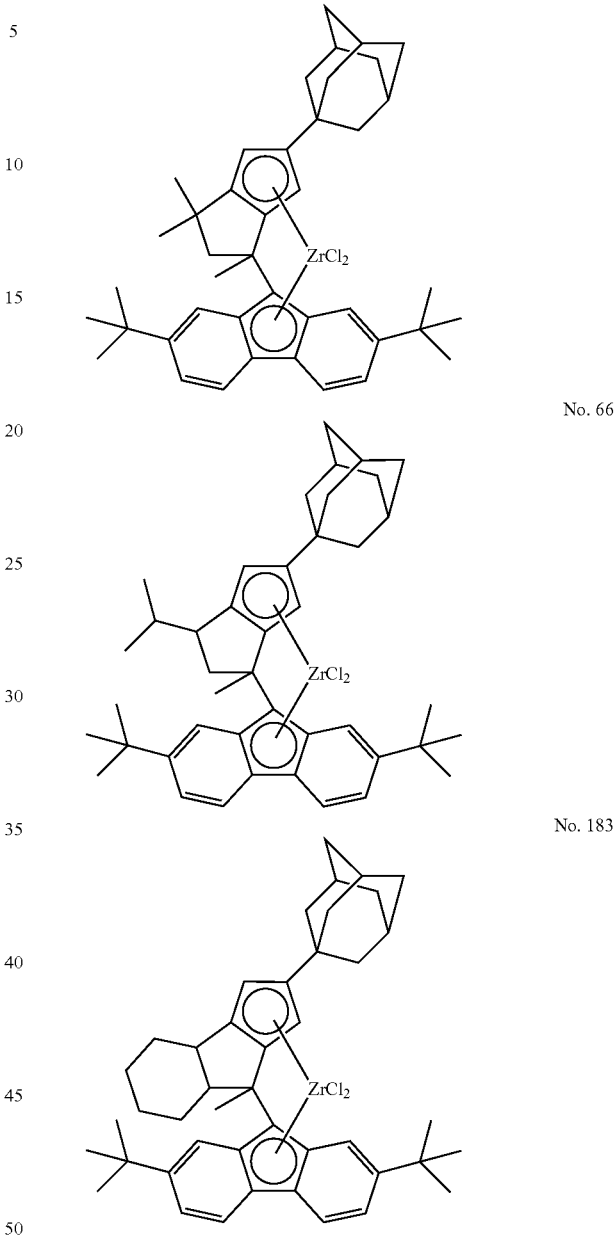

Specific examples of MQ$_j$ include ZrCl$_2$, ZrBr$_2$, ZrMe$_2$, Zr(OTs)$_2$, Zr(OMs)$_2$, Zr(OTf)$_2$, TiCl$_2$, TiBr$_2$, TiMe$_2$, Ti(OTs)$_2$, Ti(OMs)$_2$, Ti(OTf)$_2$, HfCl$_2$, HfBr$_2$, HfMe$_2$, Hf(OTs)$_2$, Hf(OMs)$_2$, and Hf(OTf)$_2$. Ts represents p-toluenesulfonyl group, Ms represents methanesulfonyl group, and Tf represents trifluoromethanesulfonyl group.

The metallocene compounds (A) of the present invention also include compounds corresponding to the above example compounds with the exception that "zirconium" is replaced with "hafnium" or "titanium" and metallocene compounds corresponding to the above example compounds with the exception that "dichloride" is replaced with "dimethyl" or "methylethyl".

[Compound (B)]

In the present invention, compound (B) is used as a component of the olefin polymerization catalyst. Compound (B) is at least one selected from (b-1) organoaluminum oxy-compound, (b-2) compound that forms an ion pair by reacting with the metallocene compound (A), and (b-3) organoaluminum compound. Among these, (b-1) organoaluminum oxy-compound is preferred in terms of efficiently producing an olefin polymer.

(Organoaluminum Oxy-Compound (b-1))

Examples of organoaluminum oxy-compound (b-1) include known conventional aluminoxanes such as a compound represented by Formula [B1] and a compound represented by Formula [B2], modified methylaluminoxane represented by Formula [B3], and boron-containing organoaluminum oxy-compound represented by Formula [B4].

[Chem. 7]

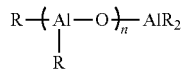
[B1]

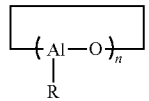
[B2]

In Formulae [B1] and [B2], R is a hydrocarbon group having 1 to 10 carbon atoms, preferably methyl group, and n is an integer, 2 or higher, preferably 3 or higher, and more preferably 10 or higher. In the present invention, methylaluminoxane, in which R in Formulae [B1] and [B2] is a methyl group, is preferably used.

[Chem. 8]

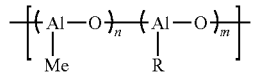
[B3]

in Formula [B3], R is a hydrocarbon group having 2 to 10 carbon atoms, and m and n are each independently an integer that is 2 or higher. A plurality of Rs may be the same or different from each other. The modified methylaluminoxane [B3] can be made using trimethylaluminum and alkylaluminum other than trimethylaluminum. The modified methylaluminoxane [B3] is commonly referred to as MMAO (modified methyl aluminoxane). Specifically, MMAO can be made using methods in U.S. Pat. No. 4,960,878 and U.S. Pat. No. 5,041,584.

Also, Tosoh Finechem Corporation commercially produces modified methylaluminoxane made by using trimethylaluminum and triisobutylaluminum (that is, R is isobutyl group in Formula [B3]) with names such as MMAO and TMAO.

MMAO is aluminoxane with improved solubility in various solvents and storage stability. Specifically, MMAO is soluble in aliphatic hydrocarbons, alicyclic hydrocarbons, and aromatic hydrocarbons unlike compounds that are insoluble or slightly soluble in benzenes such as the compounds represented by Formulae [B1] or [B2].

[Chem. 9]

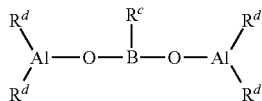
[B4]

In Formula [B4], $R^c$ is a hydrocarbon group having 1 to 10 carbon atoms. A plurality of $R^d$s are each independently a hydrogen atom, a halogen atom, or a hydrocarbon group having 1 to 10 carbon atoms. In the present invention, an olefin polymer can be produced in high temperatures as will be described later.

Therefore, a feature of the present invention is that even organoaluminum oxy-compounds insoluble or slightly insoluble in benzene can be used as example of which is cited in JP-A-H02-78687. Further, organoaluminum oxy-compounds described in JP-A-H02-167305, and aluminoxane having two or more types of alkyl groups described in JP-A-H02-24701 and JP-A-H03-103407 can also preferably be used.

Also, organoaluminum oxy-compounds that are "insoluble or slightly soluble in benzene" described above refers to organoaluminum oxy-compounds whose amount of dissolution in benzene of 60° C. is, in terms of Al atoms, usually 10 wt % or less, preferably 5 wt % or less, and particularly preferably 2 wt % or less.

In the present invention, the organoaluminum oxy-compound (b-1) as illustrated above may be used singly or two or more may be used in combination.

(Compound (b-2) that Form an Ion Pair by Reacting with Crosslinked Metallocene Compounds (A))

Examples of compound (b-2) that form an ion pair by reacting with crosslinked metallocene compounds (A) (hereinafter referred to as "ionic compounds (b-2)") include Lewis acids, ionic compounds, borane compounds, and carborane compounds cited in JP-A-H01-501950, JP-A-H01-502036, JP-A-H03-179005, JP-A-H03-179006, JP-A-H03-207703, JP-A-H03-207704, JP-A-2004-051676, and U.S. Pat. No. 5,321,106. Further examples include heteropoly compounds and isopoly compounds. Among these, ionic compound (b-2) is preferably a compound represented by General Formula [B5].

[Chem. 10]

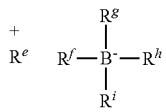
[B5]

In Formula [B5], examples of $R^{e+}$ include $H^+$, oxonium cation, carbenium cation, ammonium cation, phosphonium cation, cycloheptyltrienyl cation, and ferrocenium cation having a transition metal. $R^f$, $R^g$, $R^h$, and $R^i$ are each independently an organic group, preferably aryl group or halogen-substituted aryl group.

Examples of the above-mentioned carbenium cation include trisubstituted carbenium cations such as triphenylcarbenium cation, tris(methylphenyl)carbenium cation, and tris(dimethylphenyl)carbenium cation.

Examples of the ammonium cation include trialkylammonium cations such as trimethylammonium cation, triethylammonium cation, tri(n-propyl)ammonium cation, triisopropylammonium cation, tri(n-butyl)ammonium cation, and triisobutylammonium; N,N-dialkylanilinium cations such as N,N-dimethylanilinium cation, N,N-diethylanilinium cation, and N,N,2,4,6-pentamethylanilinium cation; and dialkylammonium cations such as diisopropylammonium cation and dicyclohexylammonium cation.

Examples of the phosphonium cation include triarylphosphonium cations such as triphenylphosphonium cation, tris(methylphenyl)phosphonium cation, and tris(dimethylphenyl)phosphonium cation. Among the above-mentioned examples, $R^{e+}$ is preferably carbenium cation or ammonium cation and particularly preferably triphenylcarbenium cation, N,N-dimethylanilinium cation, and N,N-diethylanilinium cation.

1. $R^{e+}$ is Carbenium Cation (Carbenium Salt)

Examples of carbenium salt include triphenylcarbenium tetraphenylborate, triphenylcarbenium tetrakis(pentafluorophenyl)borate, triphenylcarbenium tetrakis(3,5-ditrifluoromethylphenyl)borate, tris(4-methylphenyl)carbenium tetrakis(pentafluorophenyl)borate, and tris(3,5-dimethylphenyl)carbenium tetrakis(pentafluorophenyl)borate.

2. $R^{e+}$ is Ammonium Cation (Ammonium Salt)

Examples of ammonium salt include trialkylammonium salt, N,N-dialkylanilinium salt, and dialkylammonium salt.

Specific examples of trialkylammonium salt include triethylammonium tetraphenylborate, tripropylammonium tetraphenylborate, tri(n-butyl)ammonium tetraphenylborate, trimethylammonium tetrakis(p-tolyl)borate, trimethylammonium tetrakis(o-tolyl)borate, tri(n-butyl)ammonium tetrakis(pentafluorophenyl)borate, triethylammonium tetrakis(pentafluorophenyl)borate, tripropylammonium tetrakis(pentafluorophenyl)borate, tripropylammonium tetrakis(2,4-dimethylphenyl)borate, tri(n-butyl)ammonium tetrakis(3,5-dimethylphenyl)borate, tri(n-butyl)ammonium tetrakis(4-trifluoromethylphenyl)borate, tri(n-butyl)ammonium tetrakis(3,5-ditrifluoromethylphenyl)borate, tri(n-butyl)ammonium tetrakis(o-tolyl)borate, dioctadecylmethylammonium tetraphenylborate, dioctadecylmethylammonium tetrakis(p-tolyl)borate, dioctadecylmethylammonium tetrakis(o-tolyl)borate, dioctadecylmethylammonium tetrakis(pentafluorophenyl)borate, dioctadecylmethylammonium tetrakis(2,4-dimethylphenyl)borate, dioctadecylmethylammonium tetrakis(3,5-dimethylphenyl)borate, dioctadecylmethylammonium tetrakis(4-trifluoromethylphenyl)borate, dioctadecylmethylammonium tetrakis(3,5-ditrifluoromethylphenyl)borate, and dioctadecylmethylammonium.

Specific examples of N,N-dialkylanilium salt include N,N-dimethylanilinium tetraphenylborate, N,N-dimethylanilinium tetrakis(pentafluorophenyl)borate, N,N-dimethylanilinium tetrakis(3,5-ditrifluoromethylphenyl)borate, N,N-diethylanilinium tetraphenylborate, N,N-diethylanilinium tetrakis(pentafluorophenyl)borate, N,N-diethylanilinium tetrakis(3,5-ditrifluoromethylphenyl)borate, N,N,2,4,6-pentamethylanilinium tetraphenylborate, and N,N,2,4,6-pentamethylanilinium tetrakis(pentafluorophenyl)borate.

Specific examples of dialkylammonium salt include diisopropylammonium tetrakis(pentafluorophenyl)borate and dicyclohexylammonium tetraphenylborate.

Ionic compounds (b-2) may be used singly, or two or more may be used in combination.

(Organoaluminum Compounds (b-3))

Examples of organoaluminum compounds (b-3) include organoaluminum compound represented by General Formula [B6], and alkyl complex compounds of Group I metals and aluminum represented by General Formula [B7].

    [B6]

In Formula [B6], $R^a$ and $R^b$ are each independently a hydrocarbon group having 1 to 15 carbon atoms, preferably 1 to 4 carbon atoms, X is a halogen atom, m is a number wherein $0<m\le 3$, n is $0\le n<3$, p is $0\le p<3$, q is $0\le q<3$, and $m+n+p+q=3$.

    [B7]

In Formula [B7], $M^2$ is Li, Na, or K, and a plurality of $R^a$s are each independently a hydrocarbon group having 1 to 15 carbon atoms, preferably 1 to 4 carbon atoms.

Examples of organoaluminum compound [B6] include tri-n-alkylaluminum such as trimethylaluminum, triethylaluminum, tri-n-butylaluminum, trihexylaluminum, and trioctylaluminum; tri-branched alkylaluminum such as triisopropylaluminum, triisobutylaluminum, tri-sec-butylaluminum, tri-tert-butylaluminum, tri2-methylbutylaluminum, tri3-methylhexylaluminum, and tri2-ethylhexylaluminum; tricycloalkylaluminum such as tricyclohexylaluminum and tricyclooctylaluminum; triarylaluminum such as triphenylaluminum and tritolylaluminum; dialkylaluminum hydride such as diisopropylaluminum hydride and diisobutylaluminum hydride; alkenylaluminum such as isoprenylaluminum, represented by the formula $(i-C_4H_9)_xAl_y(C_5H_{10})_z$ (In the formula, x, y, and z are positive numbers and $z\le 2x$.); alkylaluminum alkoxide such as isobutylaluminum methoxide and isobutylaluminum ethoxide; dialkylaluminum alkoxide such as dimethylaluminym methoxide, diethylaluminum ethoxide and dibutylaluminum butoxide; alkylaluminum sesquialkoxide such as ethylaluminum sesquiethoxide and butylaluminum sesquibutoxide; partially alkoxylated alkylaluminum having average composition represented by the formula $R^a_{2.5}Al(OR^b)_{0.5}$ (In the formula, $R^a$ and $R^b$ refer to the same $R^a$ and $R^b$ in Formula [B6].); alkylaluminum aryloxide including diethylaluminum phenoxide and diethylaluminum (2,6-di-tert-butyl-4-methylphenoxide); dialkylaluminum halide such as dimethylaluminum chloride, diethylaluminum chloride, dibutylaluminum chloride, diethylaluminum bromide, and diisobutylaluminum chloride; alkylaluminum sesquihalide such as ethylaluminum sesquichloride, butylaluminum sesquichloride and ethylaluminum sesquibromide; partially halogenated alkylaluminum including alkylaluminum dihalide such as ethylaluminum dichloride; partially hydrogenated alkylaluminum including dialkylaluminum hydride such as diethylaluminum hydride and dibutylaluminum hydride, and alkylaluminum dihydride such as ethylaluminum dihydride and propylaluminum dihydride; and partially alkoxylated or partially halogenated alkylaluminum such as ethylaluminum ethoxychloride, butylaluminum butoxychldride, and ethylaluminum ethoxybromide.

Examples of alkyl complex compound [B7] include LiAl$(C_2H_5)_4$ and LiAl$(C_7H_{15})_4$. Further, compounds similar to alkyl complex compound [B7] can also be used, and the examples include organoaluminum compounds having two or more aluminum compounds combined through a nitrogen atom, such as $(C_2H_5)_2AlN(C_2H_5)Al(C_2H_5)_2$.

Organoaluminum compounds (b-3) are preferably trimethylaluminum or triisobutylaluminum because they are easy to obtain. Further, organoaluminum compounds (b-3) may be used singly, or two or more may be used in combination.

[Carrier (C)]

In the present invention, carrier (C) may be used as an olefin polymerization catalyst component. Carrier (C) is an inorganic or organic compound in the form of a granular or fine particulate solid.

(Inorganic Compound)

Examples of the inorganic compound include porous oxides, inorganic halides, clay minerals, clays (usually containing the clay minerals as main components), and ion-exchangeable layered compounds (Most clay minerals are ion-exchangeable layered compounds). Examples of porous oxides include $SiO_2$, $Al_2O_3$, MgO, ZrO, $TiO_2$, $B_2O_3$, CaO, ZnO, BaO, and $ThO_2$; and complexes and mixtures containing these oxides. Examples of these complexes and mixtures include natural or synthetic zeolites, $SiO_2$—MgO, $SiO_2$—$Al_2O_3$, $SiO_2$—$TiO_2$, $SiO_2$—$V_2O_5$, $SiO_2$—$Cr_2O_3$, $SiO_2$—Ti—MgO. Among these, porous oxides with either one or both of $SiO_2$ and $Al_2O_3$ as the main components are preferred.

The porous oxides have different properties depending on the types and production processes, but they have a particle diameter of preferably 10 to 300 μm, and more preferably 20 to 200 μm; a specific surface area of preferably 50 to 1,000 $m^2/g$, and more preferably 100 to 700 $m^2/g$; a pore volume of preferably 0.3 to 3.0 $cm^3/g$. These oxides are used after being calcined at 100 to 1,000° C., preferably at 150 to 700° C., where necessary. Examples of inorganic halides include $MgCl_2$, $MgBr_2$, $MnCl_2$, and $MnBr_2$. These inorganic halides may be used as they are or after being crushed with a ball mill or an oscillating mill. Further, the inorganic halides may be used after being dissolved in solvents such as alcohols and precipitated as fine particles with precipitating agents.

The clays, clay minerals, and ion-exchangeable layered compounds are not limited to natural products and may also be synthetic products. Also, the ion-exchangeable layered compounds are compounds having a crystal structure in which planes formed by bonds such as ionic bonds are stacked in parallel on top of one another with weak bond strength, and in which the ions contained therein are exchangeable.

Specific examples of the clays and the clay minerals include kaolin, bentonite, kibushi clay, gairome clay, allophane, hisingerite, pyrophyllite, mica such as synthetic mica, montmorillonite, vermiculite, chlorite, palygorskite, kaolinite, nacrite, dickite, hectorite, taeniolite, and halloysite; and examples of the ion-exchangeable layered compounds include ion crystalline compounds having layered crystal structures such as hexagonal closest packed structures, antimony structures, $CdCl_2$ structures, and $CdI_2$ structures. Specific examples of the ion-exchangeable layered compounds include crystalline acid salts of polyvalent metals such as α-$Zr(HAsO_4)_2 \cdot H_2O$, α-$Zr(HPO_4)_2$, α-$Zr(KPO_4)_2 \cdot 3H_2O$, α-$Ti(HPO_4)_2$, α-$Ti(HAsO_4)_2 \cdot H_2O$, α-$Sn(HPO_4)_2 \cdot H_2O$, γ-$Zr(HPO_4)_2$, γ-$Ti(HPO_4)_2$, γ-$Ti(NH_4PO_4)_2 \cdot H_2O$.

It is preferable to subject the clays and the clay minerals to chemical treatments. Any chemical treatments may be used, with examples including a treatment to remove impurities on the surface and a treatment to modify the crystal structure of the clay. Specific examples of chemical treatments include acid treatments, alkali treatments, salt treatments, and organic treatments.

Further, the spaces between the layers in the ion-exchangeable layered compounds may be enlarged by exchanging the exchangeable ions between the layers with other larger and bulkier ions utilizing the ion exchange properties. Such bulky ions serve as columns to support the layered structures and are generally called pillars. For example, the oxide columns (pillars) can be formed through the intercalation of the metal hydroxide ions below between the layers of layered compounds followed by thermal dehydration. Also, the introduction of other substances between layers of layered compounds is called intercalation.

Examples of guest compounds to be intercalated include cationic inorganic compounds such as $TiCl_4$ and $ZrCl_4$; metal alkoxides such as $Ti(OR)_4$, $Zr(OR)_4$, $PO(OR)_3$, and $B(OR)_3$ (R is a hydrocarbon group or the like); and metal hydroxide ions such as $[Al_{13}O_4(OH)_{24}]^{7+}$, $[Zr_4(OH)_{14}]^{2+}$, and $[Fe_3O(OCOCH_3)_6]^+$. These guest compounds may be used singly, or two or more may be used in combination.

Further, the intercalation of the guest compounds may be carried out in the presence of polymers obtained by hydrolysis or polycondensation of metal alkoxides such as $Si(OR)_4$, $Al(OR)_3$, and $Ge(OR)_4$ (R is a hydrocarbon group or the like), or in the presence of colloidal inorganic compounds such as $SiO_2$. Among the inorganic compounds, the clay minerals and the clays are preferable, especially montmorillionite, vermiculite, hectorite, taeniolite, and synthetic mica.

(Organic Compounds)

Examples of the organic compounds include granular or fine particulate solids with a particle diameter of 10 to 300 μm. Specific examples include (co)polymers synthesized with, as a main component, an α-olefin having 2 to 14 carbon atoms such as ethylene, propylene, 1-butene, or 4-methyl-1-pentene; (co)polymers synthesized with vinylcyclohexane or styrene as a main component; and the modified products of these polymers.

[Organic Compound Components (D)]

In the present invention, organic compound component (D) may be used as an olefin polymerization catalyst component. The organic compound component (D) is used, as needed, to improve the polymerization performance in a polymerization reaction of an α-olefin and to enhance the properties of the obtainable olefin polymers. Examples of the organic compound component (D) include alcohols, phenolic compounds, carboxylic acids, phosphorus compounds, and sulfonate salts.

<Use and Sequence of Addition of Components>

In olefin polymerization, the components may be used and added inappropriately selected manners and orders. For example, the components may be used and added as described below. In the following, the transition metal compound (A), the compound (B), the carrier (C) and the organic compound component (D) are also referred to as "components (A) to (D)".

(1) The component (A) alone is added to a polymerization reactor.

(2) The component (A) and the component (B) are added to a polymerization reactor in any order.

(3) A catalyst component, in which the component (A) is supported on the component (C), and the component (B) are added to a polymerization reactor in any order.

(4) A catalyst component, in which the component (B) is supported on the component (C), and the component are added to a polymerization reactor in any order.

(5) A catalyst component in which the component (A) and the component (B) are supported on the component (C) is added to a polymerization reactor.

In each of the methods (2) to (5), two or more of the catalyst components may be brought into contact with each other beforehand. In each of the above methods (4) and (5), in which the component (B) is supported, an unsupported component (B) may be added in any order as necessary. In this case, the components (B) may be the same or different from each other. Further, an olefin may be prepolymerized on the solid catalyst component in which the component (A) is supported on the component (C), and the solid catalyst component in which the component (A) and the component (B) are supported on the component (C). Furthermore, an additional catalyst component may be supported on the prepolymerized solid catalyst component.

[Olefin Polymer Production Method]

The production method of olefin polymers in the present invention comprises a process of polymerizing one, or two or more olefins in the presence of the olefin polymerization catalyst of the present invention at polymerization temperature of not less than 50° C. and not more than 200° C. Here, the term "polymerization" is used as a collective term including homopolymerization and copolymerization. Further, the meaning of the phrase "olefins are polymerized in the presence of the olefin polymerization catalyst" includes the embodiments in which olefins are polymerized while the components of the olefin polymerization catalyst are added to a polymerization reactor in an appropriate manner as described in the above-mentioned methods (1) to (5).

Preferably, an olefin polymer is produced by polymerizing monomer(s) comprising at least one olefin selected from α-olefin having 3 to 20 carbon atoms in the presence of the olefin polymerization catalyst of the present invention.

In the present invention, the polymerization may be carried out by any of liquid-phase polymerization methods such as solution polymerization and suspension polymerization, and gas-phase polymerization methods. Examples of inert hydrocarbon solvents used in the liquid-phase polymerization methods include aliphatic hydrocarbons such as propane, butane, pentane, hexane, heptane, octane, decane, dodecane and kerosine; alicyclic hydrocarbons such as cyclopentane, cyclohexane and methylcyclopentane; aromatic hydrocarbons such as benzene, toluene and xylene; and halogenated hydrocarbons such as ethylene chloride, chlorobenzene and dichloromethane. The inert hydrocarbon solvents may be used singly, or two or more may be used in combination. Also, the so-called bulk polymerization method may be used, in which the liquefied olefin supplied to the polymerization itself is used as the solvent.

In the polymerization of olefins using the olefin polymerization catalyst of the present invention, the components that form the olefin polymerization catalyst may be used in the following amounts. In the olefin polymerization catalyst, the contents of the components may be set as described below.

(1) in the olefin polymerization using olefin polymerization catalyst, the metallocene compound (A) is usually used in an amount of $10^{-9}$ to $10^{-1}$ mol, and preferably $10^{-8}$ to $10^{-2}$ mol per liter of the reaction volume.

(2) When the organoaluminum oxy-compound (b-1) is used as a component of the olefin polymerization catalyst, the compound (b-1) may be used in such an amount that the molar ratio [Al/M] of the aluminum atoms (Al) in the compound (b-1) to all the transition metal atoms (M) in the metallocene compound (A) is usually 0.01 to 5,000, and preferably 0.05 to 2,000.

(3) When the ionic compound (b-2) is used as a component of the olefin polymerization catalyst, the compound (b-2) may be used in such an amount that the molar ratio [(b-2)/M] of the compound (b-2) to all the transition metal atoms (M) in the metallocene compound (A) is usually 1 to 10, and preferably 1 to 5.

(4) When the organoaluminum compound (b-3) is used as a component of the olefin polymerization catalyst, the compound (b-3) may be used in such an amount that the molar ratio [(b-3)/M] of the compound (b-3) to all the transition metal atoms (N) in the metallocene compound (A) is usually 10 to 5,000, preferably 20 to 2,000.

(5) When the organic compound component (D) is used as a component of the olefin polymerization catalyst, the amount thereof may be such that, when the compound (B) is the organoaluminum oxy-compound (b-1), the molar ratio [(D)/(b-1)] of the organic compound component (D) to the compound (b-1) is usually 0.01 to 10, preferably 0.1 to 5; when the compound (B) is the ionic compound (b-2), the molar ratio [(D)/(b-2)] of the organic compound component (D) to the compound (b-2) is usually 0.01 to 10, preferably 0.1 to 5; when the compound (B) is the organoaluminum compound (b-3), the molar ratio [(D)/(b-3)] of the organic compound component (D) to the compound (b-3) is usually 0.01 to 2, preferably 0.005 to 1.

In the production process of the invention, the olefin polymerization temperature is usually 50 to 200° C., preferably 50 to 180° C., and particularly preferably 50 to 150° C. (in other words, particularly preferably a temperature at which industrial production is feasible); and the polymerization pressure is usually atmospheric pressure to 10 MPaG, and preferably atmospheric pressure to 5 MPaG. The polymerization reaction may be carried out batch wise, semi-continuously or continuously. The polymerization may be carried out in two or more stages under different reaction conditions. The molecular weight of the obtainable olefin polymers may be adjusted by hydrogen and so on in the polymerization system, by controlling the polymerization temperature, or by controlling the amount of the component (B) used.

The production process of the invention can produce olefin polymers such as propylene polymers which have high molecular weight, in such a manner that high catalytic activity is maintained even under industrially advantageous high-temperature conditions.

In particular, hydrogen is a preferred additive which may advance the polymerization activity of the catalyst and may increase or decrease the molecular weight of polymers. When hydrogen is added to the system, the amount thereof is appropriately about 0.00001 to 100 NL per 1 mol of the olefin. The hydrogen concentration in the system may be controlled by adjusting the amount of hydrogen supplied, or also by performing a reaction in the system which generates or consumes hydrogen, by separating hydrogen with use of a membrane, by discharging part of the gas containing hydrogen out of the system.

Olefin polymers synthesized by the production process of the invention may be subjected to known post treatment steps such as catalyst deactivation, residual catalyst removal step and drying step as required.

<Olefins>

The olefin supplied to the polymerization reaction in the inventive production process is at least one olefin selected from α-olefins having 3 to 20 carbon atoms.

Examples of the α-olefins having to 20 carbon atoms include linear or branched α-olefins. Examples of the linear or branched α-olefins include propylene, 1-butene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene, 1-octadecene and 1-eicosene. The olefin used is preferably supplied from at least one olefin selected from α-olefins having 3 to 10 carbon atoms, particularly preferably propylene. The α-olefins may be used singly, or two or more may be used in combination.

When propylene is used for α-olefin, it may be used together with at least one olefin A selected from ethylene and α-olefins having 4 to 20 carbons atoms as required. The olefin A which may be used together with propylene is preferably at least one selected from ethylene and α-olefins having 4 to 10 carbon atoms, of which examples include ethylene, 1-butene, 1-pentene, 3-methyl-1-butene, 1-hexene, 4-methyl-1-pentene, 3-methyl-1-pentene, 1-octene and 1-decene; in particular, is more preferably one selected from ethylene, 1-butene, 1-hexene, 4-methyl-1-pentene and 1-octene, and even more preferably ethylene. In the case of copolymerization, the combination of propylene and ethylene is the most preferred.

When propylene is used for α-olefin, propylene and at least one optional olefin A selected from ethylene and α-olefin having 4 to 20 carbon atoms are used in such amount that the propylene: olefin A ratio (by mol) is usually 1:10 to 5,000:1, and preferably 1:5 to 1,000:1.

The polymerization may be performed in the presence of at least one selected from cyclic olefins, polar group-containing olefins, hydroxyl-terminated vinyl compounds and aromatic vinyl compounds in the reaction system. Further, the polymerization may involve polyenes. Additional components such as vinylcyclohexane may be copolymerized without departing from the spirit of the invention.

Examples of the cyclic olefins include cyclopentene, cycloheptene, norbornene, 5-methyl-2-norbornene, tetracyclododecene and 2-methyl-1,4,5,8-dimethano-1,2,3,4,4a,5,8,8a-octahydronaphthalene.

Examples of the polar group-containing olefins include
α,β-unsaturated carboxylic acids such as acrylic acid, methacrylic acid, fumaric acid, maleic anhydride, itaconic acid, itaconic anhydride and bicyclo(2,2,1)-5-heptene-2,3-dicarboxylic anhydride, and metal salts thereof such as sodium salts, potassium salts, lithium salts, zinc salts, magnesium salts, calcium salts and aluminum salts;

α,β-unsaturated carboxylate esters such as methyl acrylate, ethyl acrylate, n-propyl acrylate, isopropyl acrylate, n-butyl acrylate, isobutyl acrylate, tert-butyl acrylate, 2-ethylhexyl acrylate, methyl methacrylate, ethyl methacrylate, n-propyl methacrylate, isopropyl methacrylate, n-butyl methacrylate and isobutyl methacrylate;

vinyl esters such as vinyl acetate, vinyl propionate, vinyl caproate, vinyl caprate, vinyl laurate, vinyl stearate and vinyl trifluoroacetate; and unsaturated glycidyls such as glycidyl acrylate, glycidyl methacrylate and itaconic acid monoglycidyl ester.

Examples of the hydroxyl-terminated vinyl compounds include linear hydroxyl-terminated vinyl compounds such as hydroxylated-1-butene, hydroxylated-1-pentene, hydroxylated-1-hexene, hydroxylated-1-octene, hydroxylated-1-decene, hydroxylated-1-undecene, hydroxylated-1-dodecene, hydroxylated-1-tetradecene, hydroxylated-1-hexadecene, hydroxylated-1-octadecene and hydroxylated-1-eicosene; and branched hydroxyl-terminated vinyl compounds such as hydroxylated-3-methyl-1-butene, hydroxylated-3-methyl-1-pentene, hydroxylated-4-methyl-1-pentene, hydroxylated-3-ethyl-1-pentene, hydroxylated-4,4-dimethyl-1-pentene, hydroxylated-4-methyl-1-hexene, hydroxylated-4,4-dimethyl-1-hexene, hydroxylated-4-ethyl-1-hexene and hydroxylated-3-ethyl-1-hexene.

Examples of the aromatic vinyl compounds include styrene; mono- or polyalkylstyrenes such as o-methylstyrene, m-methylstyrene, p-methylstyrene, o,p-dimethylstyrene, o-ethylstyrene, m-ethylstyrene and p-ethylstyrene; functional group-containing styrene derivatives such as methoxystyrene, ethoxystyrene, vinylbenzoic acid, methyl vinylbenzoate, vinyl benzyl acetate, hydroxystyrene, o-chlorostyrene, p-chlorostyrene and divinylbenzene; 3-phenylpropylene, 4-phenylpropylene and α-methylstyrene.

The polyenes are preferably selected from dienes and trienes. In a preferred embodiment, the polyene is used in the range of 0.0001 to 1 mol % relative to all the olefins supplied to the polymerization reaction.

Examples of the dienes include α,ω-nonconjugated dienes such as 1,4-pentadiene, 1,5-hexadiene, 1,4-hexadiene, 1,4-octadiene, 1,5-octadiene, 1,6-octadiene, 1,7-octadiene and 1,9-decadiene; nonconjugated dienes such as ethylidenenorbornene, vinylnorbornene, dicyclopentadiene, 7-methyl-1,6-octadiene and 4-ethylidene-8-methyl-1,7-nonadiene; and conjugated dienes such as butadiene and isoprene. Of these, the α,ω-nonconjugated dienes and dienes having a norbornene skeleton are preferred.

Examples of the trienes include nonconjugated trienes such as 6,10-dimethyl-1,5,9-undecatriene, 4,8-dimethyl-1,4,8-decatriene, 5,9-dimethyl-1,4,8-decatriene, 6,9-dimethyl-1,5,8-decatriene, 6,8,9-trimethyl-1,5,8-decatriene, 6-ethyl-10-methyl-1,5,9-undecatriene, 4-ethylidene-1,6-octadiene, 7-methyl-4-ethylidene-1,6-octadiene, 4-ethylidene-8-methyl-1,7-nonadiene (EMND), 7-methyl-4-ethylidene-1,6-nonadiene, 7-ethyl-4-ethylidene-1,6-nonadiene, 6,7-dimethyl-4-ethylidene-1,6-octadiene, 6,7-dimethyl-4-ethylidene-1,6-nonadiene, 4-ethylidene-1,6-decadiene, 7-methyl-4-ethylidene-1,6-decadiene, 7-methyl-6-propyl-4-ethylidene-1,6-octadiene, 4-ethylidene-1,7-nonadiene, 8-methyl-4-ethylidene-1,7-nonadiene and 4-ethylidene-1,7-undecanediene; and conjugated trienes such as 1,3,5-hexatriene. Of these, nonconjugated trienes having a double bond at an end, 4,8-dimethyl-1,4,8-decatriene and 4-ethylidene-8-methyl-1,7-nonadiene (EMND) are preferable.

The dienes or trienes may be used singly, or two or more may be used in combination. Further, the dienes and the trienes may be used in combination. Of the polyenes, the α,ω-nonconjugated dienes and the polyenes having a norbornene skeleton are preferred.

[Olefin Polymers]

According to the invention, olefin polymers may be obtained by polymerizing monomer(s) including one, or two or more olefins having 3 to 20 carbon atoms in the presence of the aforementioned olefin polymerization catalyst of the invention, which includes the novel metallocene compound having a particular structure described above. Preferably, the olefin polymers may be efficiently produced by polymerizing propylene and optionally at least one olefin A selected from ethylene and α-olefins having 4 to 20 carbon atoms.

In an embodiment, the olefin polymer of the invention is a propylene polymer containing propylene-derived structural units in the range of 50 to 100 mol %, and structural units derived from monomer(s) other than propylene, in particular, structural units derived from the above-mentioned olefin(s) A in the range of 0 to 50 mol %, wherein the total of the content of the propylene-derived structural units and the content of the structural units derived from monomer (s) other than propylene, in particular, structural units derived from the above-mentioned olefin(s) A is defined as 100 mol %. In a specific embodiment, the olefin polymer of the invention is preferably a propylene homopolymer. In another specific embodiment, the olefin polymer of the invention is preferably a copolymer of propylene and monomer (s) other than propylene, in particular, the olefin(s) A other than propylene. In case the olefin polymer is such a copolymer, the propylene polymer preferably contains propylene-derived structural units in the range of 80 to 99.5 mol %, and more preferably 90 to 99 mol %. In such a case, the propylene polymer contains structural units derived from monomer(s) other than propylene, in particular, structural units derived from the olefin(s) A other than propylene, in the range of 0.5 to 20 mol %, and more preferably 1 to 10 mol %. The olefin copolymer of which structural units derived from the olefin(s) A are in the above-described range has an excellent forming properties. The polymers may contain other structural units without departing from the spirit of the invention. The contents of these units may be determined by nuclear magnetic resonance spectroscopy or, in the case where there is a reference substance, by a method such as infrared spectroscopy.

Particularly preferred polymers are propylene homopolymers, propylene/ethylene copolymers, propylene/1-butene copolymers, propylene/ethylene/1-butene copolymers, propylene/1-octene polymers, propylene/1-hexene polymers, propylene/4-methyl-1-pentene polymers, propylene/ethylene/1-octene polymers, propylene/ethylene/1-hexene polymers and propylene/ethylene/4-methyl-1-pentene polymers. The polymers may be so-called block copolymers (impact copolymers), which are obtained by mixing or continuously producing two or more of these polymers.

Of the olefin polymers of the invention having the structural units described above, the most preferred polymers are propylene polymers substantially consisting of propylene-derived structural units, and propylene/ethylene copolymers substantially consisting of propylene-derived structural units and ethylene-derived structural units. The term "substantially" means that the propylene polymers contain 95 wt % or more of propylene-derived structural units and the propylene/ethylene copolymers contain propylene-derived structural units and ethylene-derived structural units in a total amount of 95 wt % or more.

The olefin polymers preferably have a melting point (Tm) measured by differential scanning calorimetry (DSC) of not less than 100° C. and less than 150° C., and more preferably in the range of 105° C. to 140° C., and particularly preferably in the range of 110° C. to 135° C. The application of olefin polymers of which the melting point is within the above-mentioned range to molded articles such as film results in an excellent low heat sealability.

Although the molecular weight of the olefin polymer of the invention is not particularly restricted, the melt mass-flow rate (MFR) measured at 230° C. under 2.16 kg load in accordance with ASTM D 1238 is preferably in the range of 0.1≤MFR≤150, and more preferably in the range of 0.1≤MFR≤100. The olefin polymers in the above MFR range have excellent forming properties.

In the olefin polymers of the invention, the intrinsic viscosity [η] in decalin of 135° C. is preferably 0.5 to 20 dl/g, more preferably 1.0 to 20 dl/g, and even more preferably 1.5 to 20 dl/g.

The method of producing the olefin polymers of the invention preferably requires olefin polymerization activity under hydrogen-free conditions of not less than 50 kg/mmol-M/h and not more than 1,000,000 kg/mmol-M/h. Further, it is preferable that the olefin polymers satisfy the following requirements (i) and (iii) at the same time, and more preferably, satisfy requirement (ii).

(i) The propylene content (P) is in the range of 51 mol %≤P≤100 mol %

(ii) The melting point (Tm) measured by differential scanning calorimetry (DSC) is in the range of 130° C.≤Tm≤155° C.

(iii) The intrinsic viscosity [η] in decalin of 135° C. is 1.0 (dl/g)≤[η]≤10 (dl/g)

In another embodiment of the invention, the production of the olefin olefins preferably requires olefin polymerization activity of not less than 1,000 kg/mmol-M/h and not more than 1,000,000 kg/mmol-M/h. Further, the olefin polymers preferably should satisfy the following requirements (i) and (iii) at the same time, and more preferably, satisfy requirement (ii).

(i) The ethylene content (E) is in the range of 1 mol %≤E≤10 mol %, and the propylene content (P) is in the range of 90 mol %≤P≤99 mol % (provided that (E)+(P)=100 mol %)

(ii) The melting point (Tm) measured by differential scanning calorimetry (DSC) is in the range of 110° C.≤Tm≤135° C.

(iii) The melt mass-flow rate (MFR) (g/10 min) measured under the conditions of ASTM D 1238 is in the range of 0.1≤MFR≤150.

In this embodiment, it is particularly preferable for the olefin polymerization catalyst to include the above-described carried (C).

EXAMPLES

The present invention will be described in further tail based on examples hereinbelow. However, the scope of the invention is not limited to such examples.

First of all, the methods of measuring the properties of the olefin polymers are described.

[Melting Point (Tm) and Crystallization Temperature (Tc) of Olefin Polymers]

The melting point (Tm) and the crystallization temperature (Tc) of olefin polymers were measured with DSC Pyris 1 or DSC 7 manufactured by Perkin Elmer Co., Ltd. in the following manner. A sample of approximately 5 mg was taken in a nitrogen atmosphere (20 mL/min):

(1) The sample was heated to 230° C. and was held at the temperature for 10 minutes, (2) And was cooled to 30° C. at 10° C./min, and was held at 30° C. for 1 minute.

(3) it was then heated to 230° C. at 10° C./min.

The melting point (Tm) was calculated from the peak top of the crystal melting peak observed during the heating process of (3), and the crystallization temperature (Tc) was calculated from the peak top of the crystallization peak observed during the cooling process of (2). In the case were a plurality of crystal melting peaks were observed in the olefin polymers described in the Examples and Comparative examples (for example, a peak Tm1 at a lower temperature side, a peak Tm2 at a higher temperature side), the peak at the highest temperature was assigned to the melting point (Tm) of the olefin polymers.

[Intrinsic Viscosity ([η])]

The intrinsic viscosity [η] was measured using decalin solvent at 135° C. in decalin. The granular pellets of olefin polymers (approximately 20 mg) was dissolved in the decalin solvent (15 ml), and the specific viscosity η sp was measured in the oil bath of 135° C. The decalin solution was further diluted by adding 5 ml of decalin solvent, from which the specific viscosity η sp was measured as described above. Two more dilutions were performed in the same manner. The value of η sp/C, when the concentration of olefin polymers (C) is extrapolated as zero, is defined as the intrinsic viscosity [η] of the olefin polymers.

Intrinsic viscosity [η]=lim (η sp/C) (C→0)

[MFR (Melt Flow Rate)]

MFR was measured in accordance with ASTM D 1238 (at 230° C. under 2.16 kg load)

41

[Weight-Average Molecular Weight (Mw), Number-Average Molecular Weight (Mn) and Molecular Weight Distribution (Mw/Mn)]

The weight-average molecular weight (Mw), number-average molecular weight (Mn) and molecular weight distribution (Mw/Mn) were measured with Alliance GPC-2000, a gel permeation chromatograph manufactured by Waters, as follows. For separation columns, two TSK gel GNH6-HT and two TSK gel GNH6-HTL were used, with each 7.5 mm in diameter and 300 mm in length. Column temperature was set at 140° C. In mobile phase, o-dichlorobenzene (Wako Pure Chemical Industries, Ltd.) was used, and 0.025 wt % of BHT (Takeda Pharmaceutical Company Ltd.) was used for antioxidant. The mobile phase was pumped at a flow rate of 1.0 ml/min, and the sample concentration was set at 15 mg/10 ml. 500 μl of sample solution was pumped, and differential refractometer was used for detector. Standard polystyrenes manufactured by Tosoh Corporation were used for weight-average molecular weight (Mw) of Mw<1,000 and Mw>4×10$^6$. Standard polystyrenes manufactured by Pressur Chemical were used for weight-average molecular weight (Mw) of 1,000≤Mw≤4×10$^6$. The molecular weight distribution (Mw/Mn) and various average molecular weights were converted into molecular weights of polypropylene by a universal calibration method.

[Measurement of Ethylene Content (E) and Propylene Content (P)]

With a Fourier transform infrared spectrophotometer FT/IR-610 manufactured by JASCO Corporation, the area in the vicinity of 1155 cm$^{-1}$ ascribed to the lateral vibration of the methyl group of propylene and the absorbance in the vicinity of 4325 cm$^{-1}$ ascribed to the overtone absorption due to the C—H stretching vibration were determined. From the ratio of these parameters, the ethylene content and propylene content were calculated with reference to a calibration curve. The calibration curve had been prepared using samples standardized by $^{13}$C-NMR.

[Measurement of Zirconium Content in Supported Catalysts]

The zirconium content in supported catalysts was measured with an ICP emission spectrophotometer (ICPS-8100) manufactured by Shimadzu Corporation. The sample was wet decomposed with sulfuric acid and nitric acid. A prescribed amount of the sample liquid (which had been filtered and diluted as required) was analyzed, and the zirconium content was determined based on a calibration curve prepared with standard samples having known concentrations.

[Identification of the Target Compound]

The structures of metallocene compounds obtained in Synthesis Examples were determined by methods such as 270 MHz $^1$H-NMR (GSH-270 manufactured by JEOL Ltd.) and ED-MS (SX-102A manufactured by JEOL Ltd.).

Synthesis Examples of Metallocene Compounds

The catalysts used in these Synthesis Examples may be synthesized in methods described in the following patent documents. Specific examples are JP-A-2000-212194, JP-A-2004-168744, JP-A-2004-189666, JP-A-2004-161957, JP-A-2007-302854, JP-A-2007-302853 and WO 01/027124 pamphlet.

42

Synthesis Example 1

Synthesis of Catalyst (a)

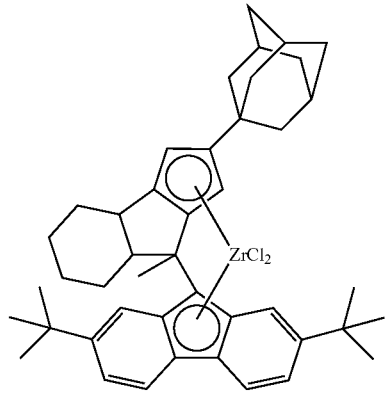

[Chem. 11]

Synthesis Example 1-1

Synthesis of Ligand (a-1)

In a nitrogen atmosphere, 2,7-di-tert-butylfluorene (2.0 g, 7.18 mmol) was dissolved in tBuOMe (150 ml) and cooled to −10° C. in an ice water bath. To this, 1.65 Mn-butyl lithium hexane solution (4.80 ml, 7.92 mmol) was slowly added, and gradually heated to 50° C. and stirred for 2 hours. The resultant mixture was again cooled to −10° C., and (3r, 5r, 7r)-1-(8-methyl-3b, 4,5,6,7,7a-hexahydro-cyclopenta[a]-inden-2-yl)adamantane (2.45 g, 8.6 mmol) was added, which was then slowly heated to room temperature and stirred at 50° C. for 2 hours. The reaction vessel was cooled in an ice water bath, and aqueous saturated ammonium chloride solution was added to extract organic matter twice with hexane. The organic layer was washed with aqueous saturated sodium hydrogen carbonate solution and saturated brine, and was dried with anhydrous magnesium sulfate and filtered. The organic layer was concentrated, and 3 ml of methylene chloride was added, which was then added dropwise to 250 ml of stirred methanol. The obtained precipitates were removed through a filter manufactured by Kiriyama, and the remains were washed with methanol. The washed powder obtained was dried under reduced pressure at 40° C. to give 1.3 g (yield of 31%) of the target compound. The compound was identified to be the target compound based on the results of the $^1$H-NMR (CDCl$_3$) and FD-MS measurements. The target compound afforded thereof is defined as ligand (a-1)

FD-MS: M/Z=584 (M$^+$)

Synthesis Example 1-2

Synthesis of Catalyst (a)

In a nitrogen atmosphere, the ligand (a-1) obtained in the Synthesis Example 1-1 (0.5 g, 0.85 mmol), toluene (40 ml) and THF (1 ml) were mixed together and cooled to −78° C. To this, 1.63 M n-butyl lithium hexane solution (1.1 ml, 1.80 mmol) was slowly added, and the resultant mixture was stirred at 50° C. for 4 hours. After cooling to room temperature, the reaction solvent was evaporated under reduced pressure, and hexane (40 ml) was added and cooled to −78° C. ZrCl$_4$ (0.20 g, 0.85 mmol) was added to this to be slowly heated to room temperature, and the resulting mixture was stirred overnight. The reaction solvent was then concentrated and hexane was added to the residue, of which the insolubles were filtered through Celite filter. After the remaining solvent was concentrated, hexane was added again and dissolved, and was settled after cooling the temperature to −30° C. The residue obtained was filtered, and was washed with hexane and dried. The target compound obtained thereof was 90 mg in amount, and 12% in yield. The compound was identified to be the target compound based on the results of the $^1$H-NMR (CDCl$_3$) and FD-MS measurements. The target compound afforded thereof is defined as catalyst (a).

$^1$H-NMR (ppm, CDCl$_3$): 7.8-6.0 (6H), 4.1-3.4 (2H), 2.3-1.0 (46H), FD-MS: M/Z=742 (M$^+$)

Synthesis Example 2

Synthesis of Catalyst (b)

[Chem. 12]

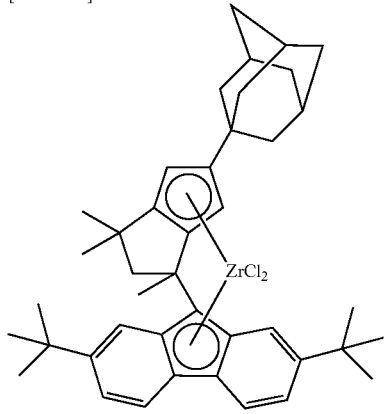

Synthesis Example 2-1

Synthesis of Ligand (b-1)

In a nitrogen atmosphere, 2,7-di-tert-butylfluorene (1.66 g, 5.96 mmol) was dissolved in tBuOMe (150 ml) and cooled to −10° C. in an ice water bath. To this, 1.63 M n-butyl lithium hexane solution (3.84 ml, 6.26 mmol) was slowly added, and gradually heated to 50° C. and stirred for 2 hours. The resultant mixture was again cooled to −10° C., and 5-adamantyl-1,1-dimethyl-3-methyl-1,2-dihydropentalene (1.87 g, 6.67 mmol) was added, which was then slowly heated to room temperature and stirred at 50° C. for 4 hours. The reaction vessel was cooled in an ice water bath, and aqueous saturated ammonium chloride solution was added to extract organic matter twice with hexane. The organic layer was washed with aqueous saturated sodium hydrogen carbonate solution and saturated brine, and was dried with anhydrous magnesium sulfate and filtered. After the condensation of the organic layer, 3 ml of methylene chloride was added, and was added dropwise to 250 ml of stirred methanol. The obtained precipitates were removed through a filter manufactured by Kiriyama, and the remains were washed with methanol. The washed powder obtained was dried under reduced pressure at 40° C. to give 2.64 g (yield of 79%) of the target compound. The compound was identified to be the target compound based on the results of the $^1$H-NMR (CDCl$_3$) and FD-MS measurements. The target compound afforded thereof is defined as ligand (b-1).

FD-MS: M/Z=558 (M$^+$)

Synthesis Example 2-2

Synthesis of Catalyst (b)

In a nitrogen atmosphere, the ligand (b-1) obtained in the Synthesis Example 2-1 (2.64 g, 4.72 mmol), toluene (156 ml) and THF (4 ml) were mixed together and cooled to −78° C. To this, 1.63 M n-butyl lithium hexane solution (6.09 ml, 9.91 mmol) was slowly added and gradually heated to room temperature. It was stirred overnight. After stirring overnight, it was heated to reach 50° C. and further stirred for 4 hours. After cooling to room temperature, the reaction solvent was evaporated under reduced pressure, and hexane (160 ml) was added and cooled to −78° C. ZrCl$_4$ (1.10 g, 4.72 mmol) was added to this to be slowly heated to room temperature, and the resultant mixture was stirred overnight. The reaction solvent was concentrated and hexane was added to the residue, of which the insolubles were filtered through Celite filter. After the remaining solvent was concentrated, hexane was added again and dissolved, and was settled after cooling the temperature to −30° C. The residue obtained was filtered, and was washed with hexane and dried. The target compound obtained thereof was 1.15 g in amount, and 34% in yield. The compound was identified to be the target compound based on the results of the $^1$H-NMR (CDCl$_3$) and FD-MS measurements. The target compound afforded thereof is defined as catalyst (a).

$^1$H-NMR (ppm, CDCl$_3$): 7.9-7.3 (6H), 6.0 (1H), 5.2 (1H), 4.0-3.9 (1H), 2.6-2.5 (1H), 2.3 (3H), 1.8-1.2 (39H), FD-MS: M/Z=716 (M$^+$)

Synthesis Example 3

Synthesis of Catalyst (c)

[Chem. 13]

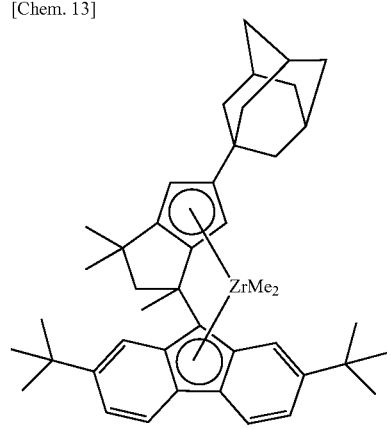

In a nitrogen atmosphere, 15 ml of diethyl ether was added to 0.2 g of catalyst (b) 0.27 mmol), and was cooled to −40° C. 0.21 ml of 3M-methyl magnesium bromide ether solution was added, and the resultant mixture was slowly heated, which was then stirred in room temperature for 48 hours. The reaction solvent was concentrated under reduced pressure, and filtration was performed with hexane. The remaining solvent was concentrated under reduced pressure, and the solids obtained from washing with hexane were concentrated under reduced pressure, thereby obtaining 50 mg of the target compound. The target compound afforded thereof is defined as catalyst (c).

$^1$H-NMR (ppm, CDCl$_3$): 7.9-7.3 (6H), 6.0 (1H), 5.0 (1H), 4.0-3.4 (1H), 2.6-1.2 (43H), −1.1~−1.6 (6H)

Synthesis Example 4

Synthesis of Catalyst (d)

[Chem. 14]

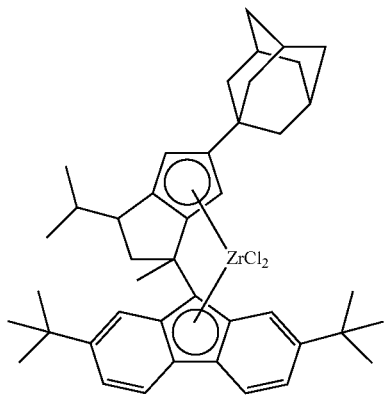

Synthesis Example 4-1

Synthesis of Ligand (d-1)

In a nitrogen atmosphere, a 100 ml three-necked flask was loaded with 682 mg of 2,7-di-tert-butylfluorene and 25 ml of tert-butyl methyl ether. 1.58 ml of 1.63 M n-butyl lithium hexane solution was added dropwise thereto over 5 minutes, in an ice water bath. It was stirred for 15 minutes in room temperature and 30 minutes at 50° C. After returning the temperature to room temperature, 793 mg of 5-adamantyl-1-isopropyl-3-methyl-1,2-dihydropentalene was further added. After stirring at 50° C. for 17 hours, the separation of organic layer was performed by adding aqueous saturated ammonium chloride solution. The aqueous layer was extracted with diethyl ether. The obtained extract was combined with the previously separated organic layer, and the combined organic layer was washed with aqueous saturated sodium hydrogen carbonate solution, water and aqueous saturated sodium chloride solution. The liquid was dried with magnesium sulfate, and the solvent was evaporated. The solids obtained were washed with methanol, thereby affording 757 mg (yield of 54%) of the target compound. The compound was identified to be the target compound based on the results of the $^1$H-NMR (CDCl$_3$) and FD-MS measurements. The target compound afforded thereof is defined as ligand

FD-MS: M/Z=572 (M$^+$)

Synthesis Example 4-2

Synthesis of Catalyst (d)

in a nitrogen atmosphere, a 100 ml Schlenk flask was loaded with 750 mg of ligand (d-1), 40 ml of toluene and 1 ml of THF. In an ice water bath, 1.65 ml of 1.63 M n-butyl lithium hexane solution was added dropwise over 5 minutes. It was then stirred at 50° C. for 2 hours. The vent was evaporated, and 55 ml of hexane was added. In a dry ice methanol cooling bath, 286 mg of ZrCl$_4$ was loaded, and the temperature was slowly returned to room temperature by stirring for 21 hours. Filtration was performed to remove the insolubles, and soluble components were extracted from hexane and dichloromethane. The solvent obtained was then concentrated and washed with hexane, and was extracted using cyclohexane. The solvent was evaporated and dried under reduced pressure, thereby affording the target compound.

Amount was 72.9 g and yield was 8.1%. The compound was identified to be the target compound based on the results of the $^1$H-NMR and FD-MS measurements. The target compound afforded thereof is defined as catalyst (d).

$^1$H-NMR (ppm, CDCl$_3$): 8.0 (1H), 7.9 (1H), 7.7 (1H), 7.6 (2H), 7.5 (1H), 6.3 (1H), 5.3 (1H), 3.8-3.7 (1H), 3.0-2.9 (1H), 2.6 (1H), 2.4 (3H), 1.9-1.6 (16H), 1.4 (9H), 1.3 (9H), 1.1-1.0 (6H), FD-MS: M/Z=730 (M$^+$)

Synthesis Example 5

Synthesis of Catalyst (e)

[Chem. 15]

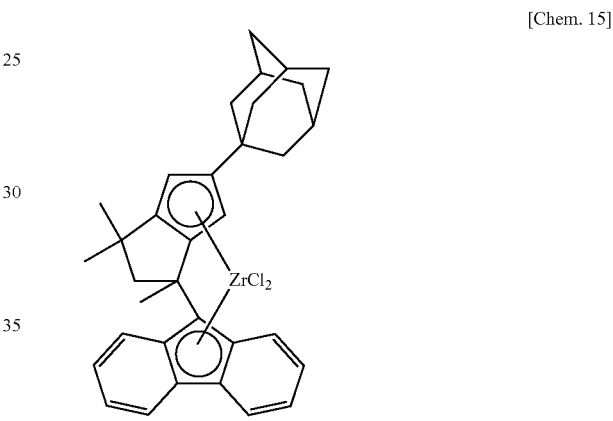

Synthesis Example 5-1

Synthesis of Ligand (e-1)

In a nitrogen atmosphere, a 100 ml three-necked flask was loaded with 1.73 g of fluorene and 150 ml of tert-butyl methyl ether. 4.0 ml of 1.63 M n-butyl lithium hexane solution was added dropwise thereto over 5 minutes, in an ice water bath. It was stirred for 30 minutes at 50° C. After returning the temperature to room temperature, 2.00 g of 5-adamantyl-1,1-dimethyl-3-methyl-1,2-dihydropentalene was added thereto, in an ice water bath. The mixture was stirred at 50° C. for 7 hours, to which aqueous saturated ammonium chloride solution was added. With this, the organic layer was separated and the aqueous layer was extracted with diethyl ether. The obtained extract was combined with the previously separated organic layer, and the combined organic layer was washed with aqueous saturated sodium hydrogen carbonate solution, water and aqueous saturated sodium chloride solution. The liquid was dried with magnesium sulfate, and the solvent was evaporated. The solids obtained were washed with methanol and acetone, thereby affording 1.58 g (yield of 57%) of the target compound. The compound was identified to be the target compound based on the results of the $^1$H-NMR and FD-MS measurements. The target compound afforded thereof is defined as ligand (e-1).
FD-MS: M/Z=446 (M⁺)

Synthesis Example 5-2

Synthesis of Catalyst (e)

In a nitrogen atmosphere, a 100 ml Schlenk flask was loaded with 750 mg of ligand (e-1), 40 ml of toluene and 1 ml of THF. 2.16 ml of 1.63M n-butyl lithium hexane solution was added dropwise thereto over 5 minutes, in an ice water bath. It was then stirred 50° C. for 4 hours. The solvent was evaporated, and 50 ml of hexane was added. 336 mg of ZrCl₄ was loaded thereto, in a dry ice-methanol cooling bath, and the temperature was slowly returned to room temperature by stirring for 16 hours. The solvent was evaporated, and soluble components were extracted from hexane and dichloromethane. The solvent obtained was then concentrated and soluble components were extracted with cyclohexane. The solvent was evaporated and dried under reduced pressure, thereby affording the target compound.

Amount was 213.5 mg and yield was 21%. The compound was identified to be the target compound based on the results of the ¹H-NMR and FD-MS measurements. The target compound afforded thereof is defined as catalyst (e).

¹H-NMR (ppm, CDCl₃): 8.1-7.2 (8H), 6.1 (1H), 5.3 (1H), 4.0 (1H), 2.7 (1H), 2.4 (3H), 2.1-1.6 (15H), 1.5-1.4 (6H), FD-MS: M/Z=604 (M⁺)

[Other Catalysts]
Catalyst (f):

[Chem. 16]

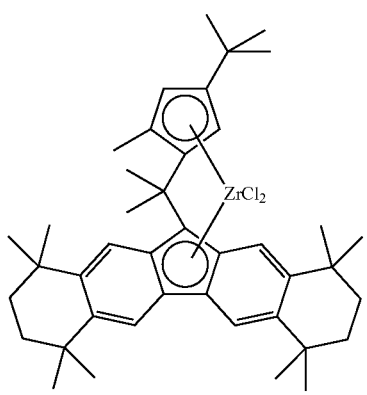

In addition to catalysts (a) to (e) obtained in the above Synthesis Examples, a compound represented by the above formula was used as catalyst (f). The catalyst (f) does not have adamantyl group unlike catalysts (a) to (e).

Example 1A in a nitrogen atmosphere, 1.8 mg (2.4 µmol) of catalyst (a) was loaded as a metallocene compound into a Schlenk flask, and was dissolved in 9.0 ml of toluene. A modified methyl aluminoxane suspension (Trade name: TMAO 341, manufactured by Tosoh Fine Chem Corporation) was added in 0.40 ml of amount (2.96M, 1.18 mmol in terms of aluminum atoms in n-hexane solution). It was stirred in room temperature for 1 hour, thereby affording 0.00025M of catalyst solution.

In a 15 ml-volume SUS autoclave that had been thoroughly purged with nitrogen, 0.4 ml of n-heptane solution of triisobutylaluminum (0.05 M, 20 µmol) and 2.5 ml of n-heptane as a polymerization solution were added. The solution was stirred at 600 RPM. The solution was then heated to 60° C., and was pressurized under propylene until the total pressure became 7 bar.

The autoclave was fed with 0.2 ml (0.05 µmol) of the catalyst solution and 0.7 ml of n-heptane, thereby initiating polymerization. After the polymerization was performed for 10 minutes at 60° C., a small amount of isobutyl alcohol was added to terminate the polymerization. The resultant slurry, in which propylene polymers generated are included, was added with 50 ml of methanol and a small amount of aqueous hydrochloric acid solution. It was stirred in room temperature for 1 hour. Next, the propylene polymers recovered by filtration were dried under reduced pressure, thereby affording 0.69 g of isotactic polypropylene.

The polymerization activity of 1 mmol of catalyst per hour of polymerization time was 131.0 kg/mmol-M/h. The melting point (Tm) of the resultant polymers was 149.3° C., the crystallization temperature (Tc) was 109.1° C., and [η] was 1.70 dl/g.

Examples 2A to 4A and Comparative Example 1A

The procedures in Example 1 were repeated, except that the metallocene compounds used as catalysts in Examples 2A to 4A and Comparative Example 1A, the amount of triisobutylaluminum and the polymerization time were changed as shown in Table 5A. The results are described in Table 5A.

TABLE 5A

| Run No. | Cat. (Catalyst) | Cat. (the Amount of Catalyst) (µmol) | Co-Cat. (Co-Catalyst) (mmol) | TIBAL (mmol) | Polymerization Temperature (° C.) | Polymerization Time (min) | Amount (g) | Activity (kg/mmol-M/h) | Tm (° C.) | Tc (° C.) | [η] (dl/g) |
|---|---|---|---|---|---|---|---|---|---|---|---|
| Ex. 1A | (a) | 0.05 | 0.025 | 0.02 | 60 | 10 | 1.092 | 131 | 149.3 | 109.1 | 1.70 |
| Ex. 2A | (b) | 0.05 | 0.025 | 0.01 | 60 | 7 | 0.476 | 81.5 | 139.5 | 101.4 | 3.02 |
| Ex. 3A | (c) | 0.05 | 0.025 | 0.01 | 60 | 5 | 0.653 | 156.8 | 137.3 | 98.6 | 2.05 |
| Ex. 4A | (d) | 0.05 | 0.025 | 0.01 | 60 | 7 | 0.564 | 96.7 | 149.4 | 108.8 | 1.77 |
| Comp. Ex. 1A | (e) | 0.05 | 0.025 | 0.01 | 60 | 10 | 0.073 | 8.8 | 141.5 | 105.8 | 2.65 |

[Chem. 17]

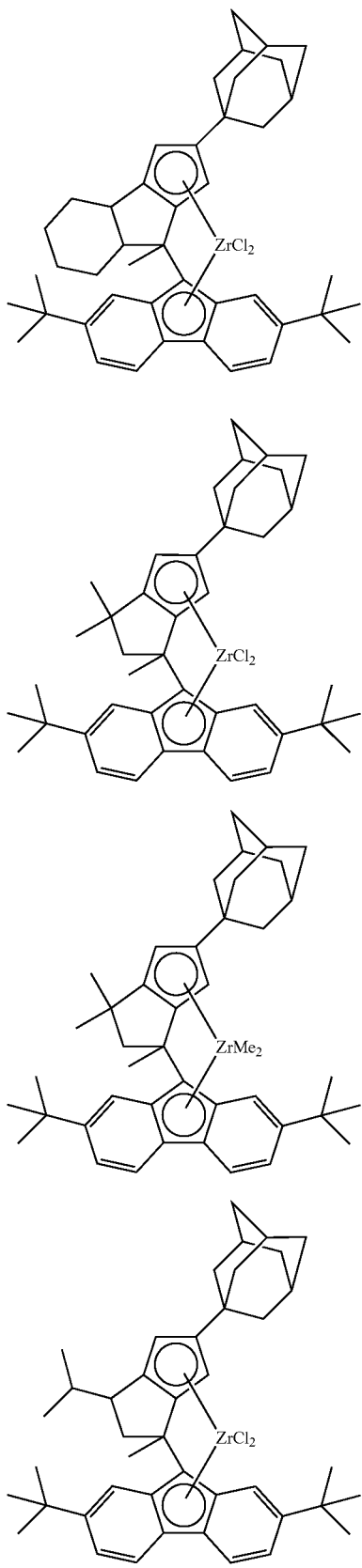

(a)

(b)

(c)

(d)

(e)

Example 13

In a nitrogen atmosphere, 0.2 µmol of catalyst (b) was loaded as a metallocene compound into a Schlenk flask, and was dissolved in toluene. A modified methyl aluminoxane suspension (Trade name: TMAO 341, manufactured by Tosoh Fine Chem Corporation) was added (2.96M, 0.05 mmol in terms of aluminum atoms in n-hexane solution). It was stirred in room temperature for 1 hour to afford a catalyst solution.

In a 15 ml-volume SUS autoclave that had been thoroughly purged with nitrogen, 0.04 mmol of n-heptane solution of triisobutylaluminum and 2.5 ml of n-heptane as a polymerization solution were added. The solution was stirred at 600 RPM. The solution was then heated to 60° C., and was pressurized under ethylene until the total pressure became 4 bar. After that, the solution was pressurized under propylene until the total pressure became 7 bar.

The autoclave was fed with the catalyst solution and 0.7 ml of n-heptane, thereby initiating polymerization. After the polymerization was performed for 10 minutes at 60° C., a small amount of isobutyl alcohol was added to terminate the polymerization. The resultant slurry, in which propylene polymers generated are included, was added with 50 ml of methanol and a small amount of aqueous hydrochloric acid solution. It was stirred in room temperature for 1 hour. Next, the ethylene-propylene copolymers recovered by filtration were dried under reduced pressure, thereby affording the target compound.

The polymerization activity of 1 mmol of catalyst per hour of polymerization time was 60 kg/mmol-M/h. The [η] was 1.51 dl/g, and the ethylene content was 37 mol %. The results are described in Table 5B.

TABLE 5B

| Run-No. | Catalyst | the Amount of Catalyst (μmol) | the Amount of Co-Catalyst (mmol) | TIBAL (mmol) | Polymerization Temperature (° C.) | Polymerization Time (min) | Activity (kg/mmol-M/h) | [η] (dl/g) | Ethylene Content (mol %) |
|---|---|---|---|---|---|---|---|---|---|
| Ex. 1B | (b) | 0.2 | 0.05 | 0.04 | 60 | 10 | 60 | 1.51 | 37 |

(Preparation of Supported Catalyst 1)—Preparation of Supported Catalyst Using Catalyst (a)

A stirring rod was attached to a 100 ml three-necked flask that had been thoroughly purged with nitrogen. To the flask, silica-supported methylaluminoxane was added. Further, 30 ml of toluene was added at room temperature. While performing stirring, there was added 4 ml of toluene solution which contained catalyst (a) as a transition metal compound. The mixture was stirred for 1 hour. The resultant slurry was filtered through a filter, and the powder on the filter was washed with 10 ml of toluene one time and with 10 ml of hexane three times. The washed powder was dried under reduced pressure for 2 hours to give a powder. The powder was mixed together with a mineral oil to form a 10.0 wt % slurry. The zirconium concentration in the supported catalyst was as shown in Table 6. The concentration of silica-supported methylaluminoxane, the amount of silica-supported methylaluminoxane added, type of catalyst used and the amount of catalyst are shown in Table 6.

(Preparation of Supported Catalyst 2 to 6)

The procedures in Preparation of supported catalyst 1 were repeated, except that the conditions shown in Table 6 were followed.

Example 1C

Propylene Polymerization

A magnetic stirrer was placed in a 50 ml branched flask that had been thoroughly purged with nitrogen. The flask was loaded with the slurry of the supported catalyst prepared in Preparation of supported catalyst 1, 1.5 mmol of a hexane solution of triisobutylaluminum (Al=1.0 M) and 5.0 ml of hexane, and was then thoroughly purged with nitrogen. The whole amount of the resultant mixture was fed into a 3,400 ml-volume SUS autoclave. Thereafter, 750 g of liquid propylene and hydrogen were supplied, and polymerization was performed at 70° C. The polymerization was terminated by cooling the autoclave and purging out propylene. The polymer obtained was dried under reduced pressure at 80° C. for 10 hours. The amounts of slurry and hydrogen, and the results are described in Table 7.

Examples 2C to 5 C and Comparative Examples 1C to 2C

The procedures in Example 1C were repeated, except that the type of catalyst, the amount of slurry, the amount of hydrogen and the polymerization time were changed to the conditions shown in Table 7.

TABLE 6

| | Silica-Supported Methylaluminoxane (Al Concentration (wt %)) | Silica-Supported Methylaluminoxane (mL) | the Type of Catalyst | the Amount of Catalyst (mg) | Zirconium Concentration in the Supported Catalyst (wt %) |
|---|---|---|---|---|---|
| Preparation of supported catalyst 1 | 19.3 | 15.4 | (a) | 20 | 0.23 |
| Preparation of supported catalyst 2 | 19.3 | 15.4 | (b) | 20 | 0.21 |
| Preparation of supported catalyst 3 | 19.3 | 20.5 | (c) | 20 | 0.24 |
| Preparation of supported catalyst 4 | 19.3 | 15.4 | (d) | 20 | 0.23 |
| Preparation of supported catalyst 5 | 19.3 | 20.5 | (e) | 20 | 0.28 |
| Preparation of supported catalyst 6 | 19.3 | 15.4 | (f) | 20 | 0.28 |

TABLE 7

| | Catalyst Preparation of Supported Catalyst (Number) | the Amount of Slurry (g) | Hydrogen NL | Hour Min | Amount g | Activity Kg/mmol-M/h | Tm ° C. | Tc ° C. | MFR g/10 min |
|---|---|---|---|---|---|---|---|---|---|
| Ex. 1C | 1 | 0.227 | 0.2 | 40 | 114.2 | 405 | 153 | 116 | 23 |
| Ex. 2C | 2 | 0.232 | 0.3 | 10 | 126.3 | 1401 | 148 | 111 | 33 |
| Ex. 3C | 3 | 0.110 | 0.2 | 40 | 204.4 | 1059 | 149 | 110 | 7 |
| Ex. 4C | 3 | 0.088 | 0.3 | 40 | 214.0 | 1392 | 149 | 110 | 29 |
| Ex. 5C | 4 | 0.143 | 0.3 | 40 | 159.4 | 669 | 152 | 116 | 130 |
| Comp. Ex. 1C | 5 | 0.439 | 0.3 | 40 | 40.5 | 45 | 145 | 111 | 3 |
| Comp. Ex. 2C | 6 | 0.143 | 0.5 | 40 | 192 | 206 | 160 | 113 | 46 |

Example 1D

Propylene/Ethylene Polymerization

A magnetic stirrer was placed in a 50 ml branched flask that had been thoroughly purged with nitrogen. The flask was loaded with the slurry of the supported catalyst prepared in Preparation of supported catalyst 1, 1.5 mmol of a hexane solution of triisobutylaluminum (Al=1.0 M) and 5.0 ml of hexane, and was then thoroughly purged with nitrogen. The whole amount of the resultant mixture was fed into a 3,400 ml-volume SUS autoclave. Thereafter, 750 g of liquid propylene, ethylene and hydrogen were supplied, and polymerization was performed at 60° C. The polymerization was terminated by cooling the autoclave and purging out propylene. The polymer obtained was dried under reduced pressure at 80° C. for 10 hours. The amounts of slurry and hydrogen and the results are described in Table 8.

Examples 2D to 5 D and Comparative Example 1D to 2D

The procedures in Example 1D were repeated, except that the type of catalyst, the amount of slurry, the amounts of ethylene and hydrogen, and the polymerization time were changed to the conditions shown in Table 8.

The invention claimed is:

1. A production method of an olefin polymer, comprising polymerizing monomer(s) comprising at least one α-olefin having 3 or more carbon atoms at not less than 50° C. and not more than 200° C. in the presence of an olefin polymerization catalyst comprising;
   (A) a crosslinked metallocene compound represented by Formula I; and
   (B) at least one compound selected from
      (b-1) an organoaluminum oxy-compound,
      (b-2) a compound that forms an ion pair by reacting with the crosslinked metallocene compound (A), and
      (b-3) an organoalunimum compound,

[Formula I]

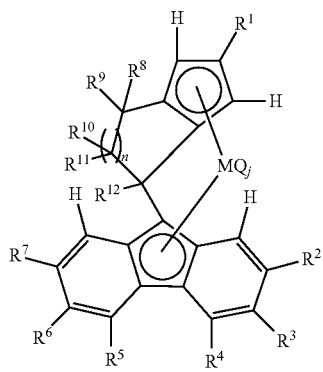

TABLE 8

| | Catalyst Preparation of supported catalyst (Number) | the Amount of Slurry (g) | Hydrogen NL | Ethylene NL | Hour min | Activity Kg/mmol-M/h | Tm ° C. | Tc ° C. | MFR g/10 Min | Ethylene Content Mol % |
|---|---|---|---|---|---|---|---|---|---|---|
| Ex. 1D | 1 | 0.141 | 0.4 | 4.5 | 10 | 1074 | 134 | 102 | 33 | ND |
| Ex. 2D | 2 | 0.086 | 0.4 | 4.5 | 10 | 1501 | 130 | 94 | 38 | ND |
| Ex. 3D | 3 | 0.074 | 0.2 | 6.9 | 10 | 1319 | 119 | 87 | 3.8 | 2.2 |
| Ex. 4D | 3 | 0.052 | 0.4 | 6.9 | 10 | 2547 | 116 | 76 | 29 | ND |
| Ex. 5D | 4 | 0.087 | 0.4 | 4.5 | 10 | 1088 | 135 | 97 | 97 | 2.2 |
| Comp. Ex. 1D | 6 | 0.034 | 0 | 2.1 | 40 | 31 | 137 | 98 | 46 | 2.3 |
| Comp. Ex. 2D | 6 | 0.034 | 0.3 | 2.1 | 40 | 211 | 148 | 107 | 105 | 1.5 |

ND: NO Data in the formula, $R^1$ is an adamantyl group derivative; $R^2$ and $R^7$ are selected from a hydrocarbon group, a silicon-containing group, or a halogen-containing hydrocarbon group; $R^3$ and $R^6$ are hydrogen atoms; $R^4$, $R^5$, $R^8$, $R^9$, $R^{10}$, $R^{11}$, and $R^{12}$ are independently selected from a hydrogen atom, a hydrocarbon group, a silicon-containing group, a halogen atom, or a halogen-containing hydrocarbon group, and adjacent substituents among $R^4$, $R^5$, $R^8$, $R^9$, $R^{10}$, $R^{11}$, and $R^{12}$ optionally form a ring; n is an integer between 1 and 3; M is a Group 4 transition metal; each Q is independently a halogen atom, a hydrocarbon group, an anionic ligand, or a neutral ligand that is bondable with a lone pair; and j is an integer between 1 and 4.

2. The production method according to claim 1, wherein in Formula I, $R^1$ is a 1-adamantyl group.

3. The production method according to claim 1, wherein in Formula I, $R^2$ and $R^7$ are hydrocarbon groups having 4 to 10 carbon atoms.

4. The production method according to claim 1, wherein in Formula I, $R^4$ and $R^5$ are hydrogen atoms.

5. The production method according to claim 1, where in Formula I, $R^{12}$ is a hydrocarbon group having 1 to 20 carbon atoms.

6. The production method according to claim 1, wherein in Formula I, $R^8$ to $R^{11}$ are hydrogen atoms or hydrocarbon groups having 1 to 20 carbon atoms.

7. The production method according to claim 1, wherein in Formula I, $R^{10}$ and $R^{11}$ are hydrogen atoms.

8. The production method according to claim 1, wherein in Formula I, $R^8$ and $R^9$ are hydrocarbon groups having 1 to 20 carbon atoms.

9. The production method according to claim 1, wherein in Formula I, n is 1.

10. The production method according to claim 1, wherein at least one of the α-olefins is propylene.

11. The production method according to claim 1, wherein the olefin polymerization activity under hydrogen-free conditions is not less than 50 kg/mmol-M/h and not more than 1,000,000 kg/mmol-M/h, and wherein the olefin polymer satisfies both of the requirements (i) and (iii) below:
(i) Propylene content (P) is 51 mol %≤P≤100 mol %;
(iii) Intrinsic viscosity [η] in decalin at 135° C. is 1.0 (dl/g)≤[η]≤10 (dl/g).

12. The production method according to claim 11, wherein the peak melting point (Tm) obtained from the differential scanning calorimetry (DSC) of the olefin polymer is 130° C.≤Tm≤155° C.

13. The production method according to claim 1, wherein the olefin polymerization activity is not less than 1,000 kg/mmol-M/h and not more than 1,000,000 kg/mmol-M/h, and wherein the olefin polymer satisfies both of the requirements (i) and (iii) below:
(i) Ethylene content (E) is 1 mol %≤E≤10 mol %, and propylene content (P) is 90 mol %≤P≤99 mol % (provided that (E)+(P)=100 mol %); and
(iii) Melt mass-flow rate (MFR; g/10 min.) measured under the conditions of ASTM D1238 is 0.1≤MFR≤150.

14. The production method according to claim 13, wherein the peak melting point (Tm) obtained from the differential scanning calorimetry (DSC) of the olefin polymer is 110° C.≤Tm≤135° C.

15. The production method according to claim 1, wherein the above olefin polymerization catalyst further comprises a carrier (C).

16. An olefin polymerization catalyst represented by Formula I,

[Formula I]

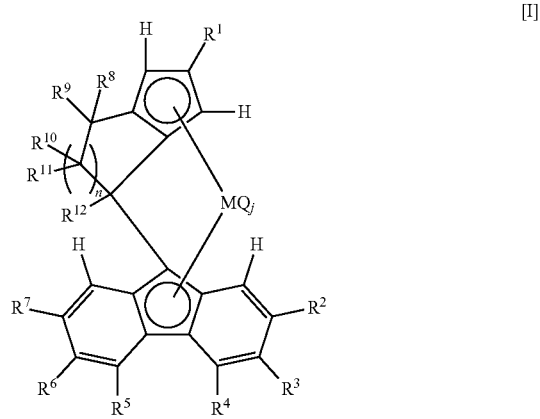

[I]

in the formula, $R^1$ is an adamantyl group derivative; $R^2$ and $R^7$ are selected from a hydrocarbon group, a silicon-containing group, or halogen-containing hydrocarbon group; $R^3$ and $R^6$ are hydrogen atoms; $R^4$, $R^5$, $R^8$, $R^9$, $R^{10}$, $R^{11}$, and $R^{12}$ are independently selected from a hydrogen atom, a hydrocarbon group, a silicon-containing group, a halogen atom, or a halogen-containing hydrocarbon group, and adjacent substituents among $R^4$, $R^5$, $R^8$, $R^9$, $R^{10}$, $R^{11}$, and $R^{12}$ optionally form a ring; n is an integer between 1 and 3; M is a Group 4 transition metal; each Q is independently a halogen atom, a hydrocarbon group, an anionic ligand, or a neutral ligand that is bondable with a lone pair; and j is an integer between 1 and 4.

17. The olefin polymerization catalyst according to claim 16, wherein in Formula I, $R^1$ is a 1-adamantyl group.

18. The olefin polymerization catalyst according to claim 16, wherein in Formula I, $R^2$ and $R^7$ are hydrocarbon groups having 4 to 10 carbon atoms.

19. The olefin polymerization catalyst according to claim 16, wherein in Formula I, $R^4$ and $R^5$ are hydrogen atoms.

20. The olefin polymerization catalyst according to claim 16, wherein in Formula I, $R^{12}$ is a hydrocarbon group having 1 to 20 carbon atoms.

21. The olefin polymerization catalyst according to claim 16, wherein in Formula I, $R^8$ to $R^{11}$ are hydrogen atoms or hydrocarbon groups having 1 to 20 carbon atoms.

22. The olefin polymerization catalyst according to claim 16, wherein in Formula I, $R^{10}$ and $R^{11}$ are hydrogen atoms.

23. The olefin polymerization catalyst according to claim 16, wherein in Formula I, $R^8$ and $R^9$ are hydrocarbon groups having 1 to 20 carbon atoms.

24. The olefin polymerization catalyst according to claim 16, wherein in Formula I, n is 1.

* * * * *